(12) United States Patent
Gjerde et al.

(10) Patent No.: US 6,503,397 B2
(45) Date of Patent: *Jan. 7, 2003

(54) NON-POLAR MEDIA FOR POLYNUCLEOTIDE SEPARATIONS

(75) Inventors: Douglas T. Gjerde, Saratoga, CA (US); Paul D. Taylor, Gilroy, CA (US)

(73) Assignee: Transgenomic, Inc., San Jose, CA (US)

( * ) Notice: Subject to any disclaimer, the term of this patent is extended or adjusted under 35 U.S.C. 154(b) by 48 days.

This patent is subject to a terminal disclaimer.

(21) Appl. No.: 09/828,315

(22) Filed: Apr. 5, 2001

(65) Prior Publication Data

US 2002/0003109 A1 Jan. 10, 2002

Related U.S. Application Data

(63) Continuation of application No. 09/399,472, filed on Sep. 20, 1999, now Pat. No. 6,258,264, which is a continuation of application No. 09/183,450, filed on Oct. 30, 1998, now Pat. No. 6,056,877, which is a continuation-in-part of application No. 09/058,337, filed on Apr. 10, 1998, now abandoned.

(60) Provisional application No. 60/069,313, filed on Dec. 5, 1997.

(51) Int. Cl.[7] .............................................. B01D 15/08
(52) U.S. Cl. ..................... 210/635; 210/656; 210/659; 210/198.2; 435/6; 536/25.4
(58) Field of Search ................. 210/635, 656, 210/659, 198.2; 435/6; 536/231, 25.4

(56) References Cited

U.S. PATENT DOCUMENTS

| | | | |
|---|---|---|---|
| 4,563,510 A | 1/1986 | Ugelstad | 526/66 |
| 4,683,202 A | 7/1987 | Mullis | 535/91 |
| 4,906,378 A | 3/1990 | Hagen et al. | 210/635 |
| 5,098,539 A | 3/1992 | Shieh | 204/182.8 |
| 5,100,547 A | 3/1992 | Hardiman et al. | 210/198.2 |
| 5,205,929 A | 4/1993 | Carr et al. | 210/198.2 |
| 5,207,914 A | 5/1993 | Lin | 210/635 |
| 5,316,680 A | 5/1994 | Frechet et al. | 210/635 |
| 5,334,310 A | 8/1994 | Frechet et al. | 210/198.2 |
| 5,338,448 A | 8/1994 | Gjerde | 210/198.2 |
| 5,453,185 A | 9/1995 | Frechet et al. | 210/198.2 |
| 5,522,994 A | 6/1996 | Frechet et al. | 210/198.2 |
| 5,585,236 A | 12/1996 | Bonn et al. | 210/635 |
| 5,616,701 A | 4/1997 | Woodard et al. | 435/5 |
| 5,772,889 A | 6/1998 | Gjerde et al. | 210/635 |
| 5,795,976 A | 8/1998 | Oefner et al. | 536/25.4 |
| 6,210,570 B1 * | 4/2001 | Holloway | 210/198.2 |
| 6,210,885 B1 * | 4/2001 | Gjerde | 210/198.2 |
| 6,238,565 B1 * | 5/2001 | Hatch | 210/635 |
| 6,372,130 B1 * | 4/2002 | Gjerde | 210/198.2 |

FOREIGN PATENT DOCUMENTS

| | | | |
|---|---|---|---|
| EP | 0 507 591 A2 | 10/1992 | 210/198.2 |
| WO | 94/11305 | 5/1994 | 210/198.2 |
| WO | 98/40395 | 9/1998 | 210/198.2 |

OTHER PUBLICATIONS

All–Chrom Newsletter Metal Components, A Potential Source Of Interference In HPLC Analysis, Alltech–Applied Science vol. 25, No. 1, Jun., 1986, pp. 1–6.

(List continued on next page.)

Primary Examiner—Ernest G. Therkorn

(57) ABSTRACT

Nonporous beads having an average diameter of about 0.5–100 microns are suitable for chromatographic separation of mixtures of polynucleotides when the beads comprise a nonporous particle which are coated with a polymer or which have substantially all surface substrate groups end-capped with a non-polar hydrocarbon or substituted hydrocarbon group. The beads provide efficient separation of polynucleotides using Matched Ion Polynucleotide Chromatography.

11 Claims, 12 Drawing Sheets

OTHER PUBLICATIONS

Apffel et al. Applications Of HPLC For The Analysis Of Doublse Stranded DNA Use Of Wide Pore Sisilca Based Materials, ISPPP '97 17th International Symposium on the Separation of Proteins, Peptides & Polynucleotides, Oct. 26–29, 1997, pp. 1–5.

Barder et al. Fast Chromatography And Nonporous Silica, LC–GC (1997) 15: 918–926, No. 10.

Berti, Dissertation, Untersuchungen Zur Ionenpaar–Umkehrphasen–Chromatographie Von DNA, Jun. 1996, pp. 52–53.

Bischoff et al, Isolation Of Specific TRNAS Using An Ionic–Hydrophobic Mixed–Mode Chromatographic Matrix, Analytical Biochemistry, 151: 526–533 (1985).

Cabrera et al. Silica Rod—A New Challenge In Fast High–Performance Liquid Chromatography Separations, Trends in Analytical Chemistry, vol. 17, No. 1, pp. 50–53, 1998.

Chen et al. High–Speed High–Performance Liquid Chromatography Of Peptides And Proteins, J. of Chromatography A (1995) 705: 3–20.

DHPLC Workshop, Stanford University, CA, pp. 32–43 (Mar. 17, 1997).

Doris et al., Quantitative Analysis Of Gene Expression By Ion–Pair High–Performance Liquid Chromatograpy, Journal of Chromatography (1998) 806: 47–60.

Engelhardt et al. Polymer Encapsulated Stationary Phases: Advantages, Properties And Selectivities, Chromatographia (1989) 27: 535–543, No. 11/12.

Erikkson et al, Separation Of DNA Restriction Fragments By Ion–Pair Chromatography, Journal of Chromatography, 359: 265–274 (1986).

Goodwin et al., Studies On The Preparation And Characterisation Of Monodisperse Polystyrene Latices, Colloid & Polymer Sci. (1974) 252: 464–471.

Green et al. HPLC Purification Of Synthetic Oligodeoxyribonucleotides Containing Base– And Backbone–Modified Sequences, BioTechniques 19:5, pp. 836–841 (Nov. 1993).

Green et al. Preparative Purification Of Supercoiled Plasmid DNA For Therapeutic Applications, BioPharm, 10:5 pp. 52–62, May 1997.

Hayward–Lester et al, Rapid Quantification Of Gene Expression By Competitive Pt–Pcr And Ion–Pair Reversed–Phase HPLC, BioTechniques, 20: 250–257 (1996).

Hayward–Lester et al., Quantification of Specific Nucleic Acids, Regulated RNA Processing and Genomic Polymorphisms Using Reversed–Phase HPLC, pp. 1–31 undated.

He et al. Fabrication Of Nanocolumns For Liquid Chromatography, Anal. Chem. (1998) 70: 3790–3797.

Heftman, Chromatography, 5th Edition, Journal of Chromatography Library—vol. 51A, Elsevier, pp. A299–A300, 1992.

Herold et al., Recovery Of Biologicaly Active Enzymes After HPLC Separation, BioChromatography, BioTechniques, vol. 10, No. 5, pp. 656–662, 1991.

Hirabayashi et al. Size–Dependent Chromatographic Separation Of Double–Stranded DNA Which Is Not Based On Gel Permeation Mode, Analytical biochemistry, 178, 336–341, 1989.

Hirabayashi, Slalom Chromatography: Size–Dependent Separation Of DNA Molecules By A Hydrodynamic Phenomenon, Biochemistry (1990) 29: 9515–9521.

http://www.transgenomic.com/html/tmha.html (May 12, 1998), pp. 1–6.

Huber et al. High–Resolution Liquid Chromatography Of Oligonucleotides On Nonporous Alkylated Styrene–Divinylbenzene Copolymers, Analytical Biochemistry, 212: 351–358 (1993).

Huber et al, High–Respolution Liquid Chromatography Of DNA Fragments On Non–Porous Poly–Styrene–Divinylbenzene) Particles, Nucleic Acid Research, vol. 21 No. 5: 1061–1066 (1993).

Huber et al, Rapid Analysis Of Biopolymers On Modified Non–Porous Polystyrene–Divinylbenzene Particles, Chromatographia, vol. 37 No. 11/12; 653–658 (Dec. 1993).

Huber et al, Rapid And Accurate Sizing Of DNA Fragments By Ion–Pair Chromatography On Alkylated Nonporous Poly(Styrene–DivinylBenzene) Particles, Analytical Chemistry, 67: 578–585 (1995).

Huber et al., Micropellicular Stationary Phases For High–Performance Liquid Chromatography Of Double–Stranded DNA, J. of Chromatography A (1998) 806:1–27.

Iler et al. The Chemistry Of Silica (1979) John Wiley & Sons, New York, pp. 566–569.

Issaq et al. Enthalpy And Entropy Effects For Hologous Solutes In HPLC With Alkyl Chain Bonded Phases, J. of Liquid Chromatography (1989) 12(11): 2067–2082.

Jinno et al. Planarity Recognition Of Large Polycyclic Aromatic Hydrocarbons By Various Octadecylsilica Stationary Phasees In Non–Aqueous RPLC, Chromatographia, vol. 27, No. 7/8, pp. 285–291, Apr. 1989.

Kato et al. Separation Of DNA Restriction Fragments By High–Preformance Ion–Exchange Chromatography On A Non–Porous Ion Exchanger, Journal of Chromatography, 478, 264–268, 1989.

Kwiatkowski et al, Use Of RP Ion Pair Chromatography To Fractionate And Purify DNA Fragments And Monomeric Components Of RNA, Acta Chemica scandinavica B, 38, 9, 721–733, (1984).

Liu et al. Denaturing High Performance Liquid Chromatography (DHPLC) Used In The Detection Of Germline And Somatic Mutaions, Nucleic Acid Research, vol. 26 No. 6: 1396–1400 (1998).

Maa et al, Rapid High–Performance Liquid Chromatography Of Ncleic Acids With Polystyrene–Based Micropellicular Anion Exchangers, Journal of Chromatography. 508 (1990) 61–73.

Melander et al., Mobile Phase Effects In Reversed–Phase Chromatography, J. of Chromatography (1979) 185: 99–109.

Mhatre et al., Interfacing Gradient Elution Ion–Exchange Chromatography (IEC) And Low Angle Laser Light Scattering Photometry (Lalls) For Analysis Of Proteins, J. Chromatography (1991) pp. 1–20.

Moriyama et al. New RP HPLC Column For Oligonucleotide Separation, Journal of Chromatography, 445, 225–233, (1988).

Nahum et al. Surface Silnols In Silica–Bonded Hydrocarbonaceous Stationary Phases, J. of Chromatography (1981) 203: 53–63.

Nakanishi et al. Double Pore Silica Gel Monolith Applied To Liquid Chromatography, J. Sol–Gel Science & Technology, vol. 8, pp. 547–552, 1997.

Nakanishi et al., Phase Separation In Silica Sol–Gel System Containing Poly(Ethylene Oxide), Bull. Chem. Soc. Jpn. (1994) 67: 1327–1335.

Oefner et al. Poster Symposium—Session 29 Comparative DNA Sequencing By Denaturing High–Performance Liquid Chromatography (DHLPC), Am. J. Human Genet. Oct. 1995, 57:A66.

Ohmiya et al., Separation Of DNA Fragments By High–Resolution Ion–Exchange Chromatography On A Nonporous QA Column, Analytical Biochemistry, 189, 126–130 (1990).

Petro et al, Molded Monolithic Rod Of Macrophorous Poly(Styrene–Co–Divinylbenzene) As A Separation Medium For HPLC Of Synthetic Polymers . . . , Analytical Chemistry. 68: 315–321 (1996).

Poole et al. Chromatography Today (1991) Elsevier, New York, pp. 313–342.

Pretorius et al., A New Concept For High–Speed Liquid Chromatography, J. of Chromatography, 99 (1974) 23–30.

Saiki et al., Enzymatic Amplification Of β–Globin Genomic Sequences And Restriction Site Analysis For Diagnosis Of Sickle Cell Anemia, Science (1985) 230: 1350–1354.

Schoburg et al. Immobilization Of Stationary Liquids In Reversed– And Normal–Phase Liquid Chromatography, J. of Chromatography (1983) 282: 27–39.

Schoburg et al. Immobilization Of Stationary Liquids Of Silica Particles By Y–Radiation. Chromatographia (1984) 18: 265–274, No. 5.

Snyder et al, Introduction To Modern Liquid Chromatography, pp. 173–174, 274–275, John Wiley & Sons, Inc. New York (1979).

Stober et al. Controlled Growth Of Monodisperse Silica Spheres In The Micron Size Range, (1968) J. of Coll. and Interface Science 26: 62–69.

Ugelstad et al, Swelling Of Oligomer–Polymer Particles. New Methods Of Preparation Of Emulsions And Polymer Dispersions, Advances in Colloid and Interface Science, 13 (1980) 101–140.

Wang et al, Reversed–Phase Chromatography Of Small Molecules And Peptides On A Continous Rod Of Macroporous Poly(Styrene–Codivinylbenzene), Journal of Chromatography, No. 669: 230–235 (1994).

Wheals, Chemically Bonded Phases For Liquid Chromatography, J. of Chromatography (1975) 107: 402–407.

Yau et al., Modern Size–Exclusion Liquid Chromatography, John Wiley & Sons, 1979, New York pp. 343–381.

* cited by examiner

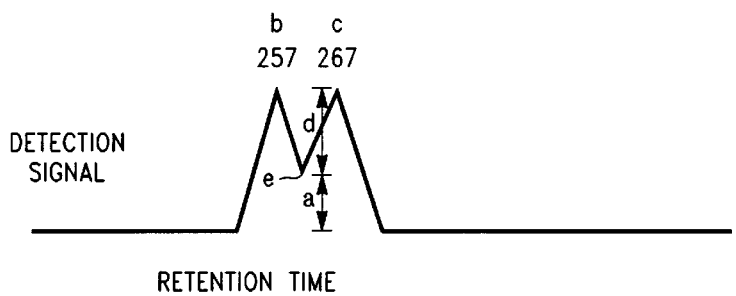
FIG.—1
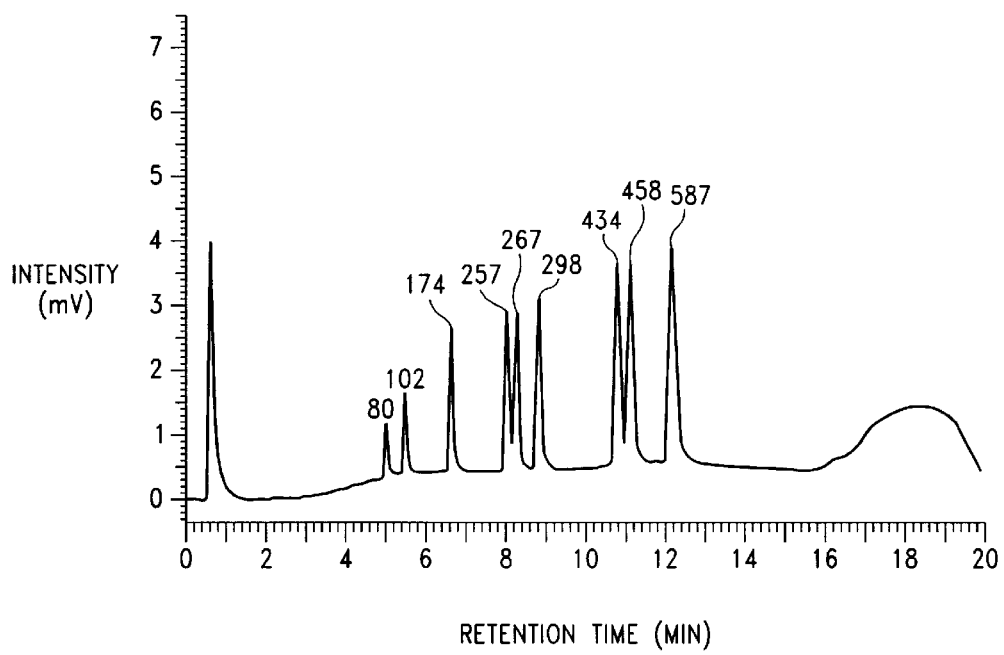
FIG.—4

NON-POLAR MEDIA FOR POLYNUCLEOTIDE SEPARATIONS

CROSS-REFERENCE TO RELATED APPLICATIONS

This application is a continuation application of U.S. patent application Ser. No. 09/399,472, filed Sep. 20, 1999 (now U.S. Pat. No. 6,258,264), which is a continuation of U.S. patent application Ser. No. 09/183,450, filed Oct. 30, 1998 (now U.S. Pat. No. 6,056,877), which is a continuation-in-part application of U.S. patent application Ser. No. 09/058,337, filed Apr. 10, 1998 (now abandoned), which claims the benefit of U.S. application Ser. No. 60/069,313, filed Dec. 5, 1997, all of which are commonly assigned and are hereby incorporated by reference in their entirety. This application is a regular U.S. Patent Application under 35 U.S.C. § 111(a) and 37C.F.R. § 1.53(b).

FIELD OF THE INVENTION

The present invention is directed to the separation of polynucleotides using a separation medium having non-polar surfaces, such as the surfaces of nonporous beads or surfaces of interstitial spaces within a molded monolith (e.g., a derivatized silica monolith), which surfaces are substantially free from contamination with multivalent cations. More specifically, the invention is directed to the chromatographic separation of both single stranded and double stranded polynucleotides by chromatography using a nonporous separation medium, where the medium is either organic or inorganic material which is coated with a polymer, or non-polar substituted polymer, and/or which has substantially all surface substrate groups substituted with a non-polar hydrocarbon or non-ionic substituted hydrocarbon.

BACKGROUND OF THE INVENTION

Separations of polynucleotides such as DNA have been traditionally performed using slab gel electrophoresis or capillary electrophoresis. However, liquid chromatographic separations of polynucleotides are becoming more important because of the ability to automate the analysis and to collect fractions after they have been separated. Therefore, columns for polynucleotide separation by liquid chromatography (LC) are becoming more important.

Silica-based columns are by far the most common LC columns. Of these, reverse phase silica-based columns are preferred because they have high separation efficiencies, are mechanically stable, and a variety of functional groups can be easily attached for a variety of column selectivities.

Although silica-based reverse phase column materials have performed adequately for separating single stranded DNA, these materials have not performed well for separating double stranded DNA. The peaks from double stranded DNA separations using silica-based materials are badly shaped or broad, or the double stranded DNA may not even elute. Separations can take up to several hours, or the resolution, peak symmetry, and sensitivity of the separation are poor.

High quality materials for DNA separations have been based on polymeric substrates, as disclosed in U.S. Pat. No. 5,585,236 to Bonn (1966). There exists a need for silica-based column packing material and other materials that are suitable for separation of double stranded DNA.

SUMMARY OF THE INVENTION

Accordingly, one object of the present invention is to provide a chromatographic method for separating polynucleotides with improved separation and efficiency. Another object is to provide improved non-polar separation media for the separation of polynucleotides.

These and other objects of the invention, which will become apparent from reading the following specification, have been achieved by the method of the present invention in which polynucleotides are separated using a nonporous separation medium such as beads or a molded monolith (e.g., a silica gel monolith), where the medium comprises either organic or inorganic material which is coated with a polymer, or non-polar substituted polymer, and/or which has substantially all surface substrate groups substituted with a non-polar hydrocarbon or non-ionic substituted hydrocarbon.

In one aspect, the invention is a method for separating a mixture of polynucleotides comprising applying a mixture of polynucleotides having up to 1500 base pairs to a separation medium, the separation surfaces of the medium coated with a hydrocarbon or non-polar hydrocarbon substituted polymer, or having substantially all polar groups reacted with a non-polar hydrocarbon or substituted hydrocarbon group, wherein said surfaces are non-polar; and eluting the polynucleotides. The separation medium can be enclosed in a column. Examples of non-polar surfaces include the surfaces of beads such as nonporous particles and the surfaces of intersitital spaces within a monolith (e.g., a silica gel monolith), which surfaces are coated with a hydrocarbon or non-polar substituted polymer or having substantially all surface substrate groups reacted with a non-polar hydrocarbon or substituted hydrocarbon group. In the preferred embodiment, precautions are taken during the production of the medium so that it is substantially free of multivalent cation contaminants and the medium is treated, for example by an acid wash treatment and/or treatment with multivalent cation binding agent, to substantially remove any residual surface metal contaminants. The preferred separation medium is characterized by having a DNA Separation Factor (defined hereinbelow) of at least 0.05. The preferred medium is characterized by having a Mutation Separation Factor (as defined hereinbelow) of at least 0.1. In a preferred embodiment, the separation is made by Matched Ion Polynucleotide Chromatography (MIPC, as defined hereinbelow). The elution step preferably uses a mobile phase containing a counterion agent and a water-soluble organic solvent. Examples of a suitable organic solvent include alcohol, nitrite, dimethylformamide, tetrahydrofuran, ester, ether, and mixtures of one or more thereof, e.g., methanol, ethanol, 2-propanol, 1-propanol, tetrahydrofuran, ethyl acetate, acetonitrile. The most preferred organic solvent is acetonitrile. The counterion agent is preferably selected from the group consisting of lower primary amine, lower secondary amine, lower tertiary amine, lower trialkyammonium salt, quaternary ammonium salt, and mixtures of one or more thereof. Non-limiting examples of counterion agents include octylammonium acetate, octyldimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, and mixtures of any one or more of the above. The counterion agent includes an anion, e.g., acetate, carbonate, bicarbonate, phosphate, sulfate, nitrate, propionate, formate, chloride, perchlorate, or bromide. The most preferred counterion agent is triethylammonium acetate or triethylammonium hexafluoroisopropyl alcohol.

One embodiment of the invention provides a method for separating a mixture of polynucleotides, comprising applying a mixture of polynucleotides having up to 1500 base pairs to separation beads having non-polar surfaces, and eluting said mixture of polynucleotides. In a particular embodiment of the separation medium, the invention provides a method for separating a mixture of polynucleotides comprising applying a mixture of polynucleotides having up to 1500 base pairs through a separation column containing beads which are substantially free from contamination with multivalent cations and having an average diameter of 0.5 to 100 microns, and eluting the mixture of polynucleotides. In one embodiment, the beads comprise nonporous particles coated with a hydrocarbon or non-polar substituted polymer or having substantially all surface substrate groups reacted with a non-polar hydrocarbon or substituted hydrocarbon group. The beads preferably have an average diameter of about 1–5 microns. In the preferred embodiment, precautions are taken during the production of the beads so that they are substantially free of multivalent cation contaminants and the beads are treated, for example, by an acid wash treatment and/or treatment with multivalent cation binding agent, to remove any residual surface metal contaminants. The beads of the invention are characterized by having a DNA Separation Factor of at least 0.05. In a preferred embodiment, the beads are characterized by having a DNA Separation Factor of at least 0.5. Also in a preferred embodiment, the beads are characterized by having a Mutation Separation Factor of at least 0.1. In one embodiment, the beads are used in a capillary column to separate a mixture of polynucleotides by capillary electrochromatography. In other embodiments, the beads are used to separate the mixture by thin-layer chromatography or by high-speed thin-layer chromatography. The separation is preferably by MIPC. The beads preferably have an average diameter of about 1–5 microns. The nonporous particle is preferably selected from silica, silica carbide, silica nitrite, titanium oxide, aluminum oxide, zirconium oxide, carbon, insoluble polysaccharides such as cellulose, and diatomaceous earth, or any of these materials that have been modified to be nonporous. The nonporous particle is most preferably silica, which preferably is substantially free from underivatized silanol groups. The particles can be prepared by noncovalently bonded coatings, covalently bonded coatings, or reaction of the silanol groups with hydrocarbon groups.

The nonporous particle can be coated with a polymer. The polymer is preferably selected from polystyrenes, polymethacrylates, polyethylenes, polyurethanes, polypropylenes, polyamides, cellulose, polydimethyl siloxane, and polydialkyl siloxane. The polymer is optionally unsubstituted or substituted with hydrocarbon groups or other groups having nonionic substituents. The polymer can be optionally substituted with hydrocarbon groups having from 1 to 1,000,000 carbons, the hydrocarbon groups optionally being alkyl groups with from 1 to 100 carbons and preferably from 1 to 24 carbons. Hydrocarbon groups from 24 to 1,000,000 are described herein as hydrocarbon polymers and have the constituency of hydrocarbon groups as defined herein.

The reaction of organosilanols (e.g. $HO-Si-R_3$) or alkoxy- (e.g., $RO-Si-R_3$) silanes with silica supports without polymerization can also produce good packings. The method produces a dense monolayer of functional groups of alkyl or alkylsubstituted, ester, cyano, and other nonionic groups. The use of monofunctional dimethyl silanes ($X-Si(CH_3)_2-R$) provides a homogeneous organic coating with a minimum of residual Si—OH groups. Monochlorosilane reagents are preferred, if the required organic functionality can be prepared. These reactions are reproducible and provide high quality packing materials. Unreacted, accessible silanols can be left after the initial reaction. The nonporous particle is preferably endcapped with a tri(lower alkyl)chlorosilane (preferably a trimethylchlorosilane) to block residual reactive silanol sites following the coating or hydrocarbon substitution. Alternatively, all of the silanol sites can be reacted with an excess of the endcapping reagent to extinguish all reactive silanol groups. Endcapping to the nonporous particle can be effected by reaction of the nonporous particle with the corresponding hydrocarbon substituted halosilane, such as trialkyl chlorosilane (eg. trimethyl chlorosilane) or by reaction with the corresponding hydrocarbon substituted disilazane, such as dichloro-tetraalkyl-disilazane (eg. dichloro-tetramethyl-disilazane).

The method of the present invention can be used to separate double stranded polynucleotides having up to about 1500 to 2000 base pairs. In many cases, the method is used to separate polynucleotides having up to 600 bases or base pairs, or which have up to 5 to 80 bases or base pairs.

The method is performed at a temperature within the range of 20° C. to 90° C. The flow-rate of the mobile phase is preferably adjusted to yield a back-pressure not greater than 10,000 psi. The method also preferably employs an organic solvent and more preferably an organic solvent that is water soluble. The solvent is preferably selected from the group consisting of alcohols, nitrites, dimethylformamide, esters, and ethers. The method also preferably employs a counterion agent selected from trialkylamine acetate, trialkylamine carbonate, and trialkylamine phosphate. The most preferred counterion agent is triethylammonium acetate or triethylammonium hexafluoroisopropyl alcohol.

In addition to the beads or other medium being substantially metal-free, Applicants have also found, that to achieve optimum peak separation, the inner surfaces of the column (or other container) and all process solutions held within the separation system or flowing through the system are preferably substantially free of multivalent cation contaminants. The method preferably comprises supplying and feeding solutions entering the separation column with components having process solution-contacting surfaces which contact process solutions held therein or flowing therethrough. The process solution-contacting surfaces are material which does not release multivalent cations into aqueous solutions held therein or flowing therethrough, so that the column and its contents are protected from multivalent cation contamination The process solution-contacting surfaces are preferably material selected from the group consisting of titanium, coated stainless steel, passivated stainless steel, and organic polymer. Multivalent cations in mobile phase solutions and sample solutions entering the column are also preferably removed by contacting the solutions with multivalent cation capture resin before the solutions enter the column so as to protect the separation medium from multivalent cation contamination. The multivalent capture resin is selected from cation exchange resin and chelating resin. The column and process solutions held therein or flowing therethrough are preferably substantially free of multivalent cation contaminants. The polynucleotides are separated by Matched Ion Polynucleotide Chromatography.

Also disclosed herein is a method for separating a mixture of polynucleotides, comprising flowing a mixture of polynucleotides having up to 1500 base pairs through a separation column containing beads having an average diameter of 0.5 to 100 microns, and separating the mixture of polynucleotides by Matched Ion Polynucleotide Chromatography. The beads comprise nonporous particles coated with a polymer or having substantially all surface substrate groups reacted and/or endcapped with a non-polar hydrocarbon or substituted hydrocarbon group. The beads are characterized by having a DNA Separation Factor of at least 0.05.

Also disclosed herein is a bead comprising a nonporous particle coated with a polymer. The bead has an average diameter of 0.5 to 100 microns and is characterized by having a DNA Separation Factor of at least 0.05. In a preferred embodiment, the bead is characterized by having a DNA Separation Factor of at least 0.5. The preferred bead is characterized by having a Mutation Separation Factor of at least 0.1. The bead preferably has a diameter of about 1–5 microns. The nonporous particle is preferably selected from silica, silica carbide, silica nitrite, titanium oxide, aluminum oxide, zirconium oxide, carbon, insoluble polysaccharides such as cellulose, and diatomaceous earth, or any of these materials that have been modified to be nonporous. The nonporous particle is most preferably silica, which preferably has minimum silanol groups. The polymer is preferably selected from polystyrene, polymethacrylate, polyethylene, polyurethane, polypropylene, polyamide, cellulose, polydimethyl siloxane, and polydialkyl siloxane, and is preferably unsubstituted, alkylated, or alkyl or aryl substituted, or alkylated with a substituted alkyl group methyl-substituted, or ethyl-substituted. The polymer can be alkylated with alkyl groups having 1–22 carbon atoms, preferably, 8–18 carbon atoms.

Also disclosed herein is a bead comprising a nonporous particle having substantially all surface substrate groups reacted with a hydrocarbon group and then endcapped with a non-polar hydrocarbon or substituted hydrocarbon group, preferably a tri(lower alkyl)chlorosilane or tetra(lower alkyl)dichlorodisilazane. The bead has an average diameter of 0.5 to 100 microns and is characterized by having a DNA Separation Factor of at least 0.05. The bead preferably has a diameter of about 1–5 microns.

The nonporous particle is preferably selected from silica, silica carbide, silica nitrite, titanium oxide, aluminum oxide, zirconium oxide, carbon, insoluble polysaccharides such as cellulose, and diatomaceous earth, or any of these materials that have been modified to be nonporous. The nonporous particle is most preferably silica, which preferably has minimum silanol groups. Endcapping of the nonporous particle can be effected by reaction of the nonporous particle with trimethyl chlorosilane or dichloro-tetraisopropyldisilazane.

In a still further aspect, the invention is a method for separating a mixture of polynucleotides comprising applying a mixture of polynucleotides having up to 1500 base pairs to a monolith having non-polar separation surfaces, and eluting the polynucleotides. The monolith can be enclosed in a column or other containment system, such as a cartridge. In a preferred embodiment, the monolith is a silica gel monolith. The non-polar separation surfaces include the surfaces of intersitital spaces within the monolith, which surfaces are coated with a hydrocarbon or non-polar substituted polymer or having substantially all surface substrate groups reacted with a non-polar hydrocarbon or substituted hydrocarbon group. An example of a suitable monolith is one which is polyfunctionally derivatized with octadecysilyl groups. In the preferred embodiment, precautions are taken during the production of the monolith so that it is substantially free of multivalent cation contaminants and the monolith is treated, for example by an acid wash treatment and/or treatment with multivalent cation binding agent, to substantially remove any residual surface metal contaminants. The preferred monolith is characterized by having a DNA Separation Factor of at least 0.05. The preferred monolith is characterized by having a Mutation Separation Factor of at least 0.1. In a preferred embodiment, the separation is made by Matched Ion Polynucleotide Chromatography. The elution step preferably uses a mobile phase containing a counterion agent and a water-soluble organic solvent. Examples of a suitable organic solvent include alcohol, nitrile, dimethylformamide, tetrahydrofuran, ester, ether, and mixtures of one or more thereof, e.g., methanol, ethanol, 2-propanol, 1-propanol, tetrahydrofuran, ethyl acetate, acetonitrile. The most preferred organic solvent is acetonitrile. The counterion agent is preferably selected from the group consisting of lower primary amine, lower secondary amine, lower tertiary amine, lower trialkyammonium salt, quaternary ammonium salt, ahd mixtures of one or more thereof. Non-limiting examples of counterion agents include octylammonium acetate, octyldimethylammonium acetate, decylammonium acetate, octadecylammonium acetate, pyridiniumammonium acetate, cyclohexylammonium acetate, diethylammonium acetate, propylethylammonium acetate, propyidiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, and mixtures of any one or more of the above. The counterion agent includes an anion, e.g., acetate, carbonate, bicarbonate, phosphate, sulfate, nitrate, propionate, formate, chloride, perchlorate, or bromide. The most preferred counterion agent is triethylammonium acetate or triethylammonium hexafluoroisopropyl alcohol.

In a yet further aspect, the invention provides a monolith having non-polar separation surfaces which are substantially free from contamination with multivalent cations. The monolith can be enclosed in a column or other containment system, such as a cartridge. The non-polar separation surfaces include the surfaces of interstitial spaces within the monolith (e.g., a silica monolith), which surfaces are coated with a hydrocarbon or non-polar substituted polymer or having substantially all surface substrate groups reacted with a non-polar hydrocarbon or substituted hydrocarbon group. An example of a suitable monolith is one which is derivatized with polyfunctionally derivatized octadecylsilyl groups. In the preferred embodiment, precautions are taken during the production of the monolith so that it is substantially free of multivalent cation contaminants and the monolith is treated, for example by an acid wash treatment and/or treatment with multivalent cation binding agent, to remove any residual surface metal contaminants. The preferred monolith is characterized by having a DNA Separation Factor of at least 0.05. The preferred monolith is characterized by having a Mutation Separation Factor of at least 0.1.

In addition to the beads (or other media) themselves being substantially metal-free, Applicants have also found that to achieve optimum peak separation the inner surfaces of the separation column (or other container) and all process solutions held within the column or flowing through the column are preferably substantially free of multivalent cation contaminants. This can be achieved by supplying and feeding solutions entering the separation column with components which have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, and organic polymer. For additional protection, multivalent cations in mobile phase solutions and sample solutions entering the column can be removed by contacting these solutions with multivalent cation capture resin before the solutions enter the column to protect the separation medium from multivalent cation contamination. The multivalent capture resin is preferably cation exchange resin and/or chelating resin.

In another aspect, the present invention is a method for treating the non-polar surfaces of a medium used for separating polynculeotides, such as the surfaces of beads in a MIPC column or the surfaces of interstitial spaces in a monolith, in order to improve the resolution of polynucleotides, such as dsDNA, separated on said surfaces. This treatment includes contacting the surface with a solution containing a multivalent cation binding agent. In a preferred embodiment, the solution has a temperature of about 50° C. to 90° C. An example of this treatment includes flowing a solution containing a multivalent cation binding agent through a MIPC column, wherein the solution has a temperature of about 50° C. to 90° C. The preferred temperature is about 70° C. to 80° C. In a preferred embodiment, the multivalent cation binding agent is a coordination compound, examples of which include water-soluble chelating agents and crown ethers. Specific examples include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, ethylenediaminetetraacetic acid (EDTA), metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. However, the most preferred chelating agent is EDTA. In this aspect of the invention, the solution preferably includes an organic solvent as exemplified by alcohol, nitrile, dimethylformamide, tetrahydrofuran, ester, ether, and mixtures thereof. Examples of suitable solvents include methanol, ethanol, 2-propanol, 1-propanol, tetrahydrofuran, ethyl acetate, acetonitrile, and mixtures thereof. The most preferred organic solvent is acetonitrile. In one embodiment, the solution can include a counterion agent such as lower primary, secondary and tertiary amines, and lower trialkyammonium salts, or quaternary ammonium salts. More specifically, the counterion agent can be octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, tetrabutylammonium acetate, and mixtures of any one or more of the above. The counterion agent includes an anion, e.g., acetate, carbonate, bicarbonate, phosphate, sulfate, nitrate, propionate, formate, chloride, perchlorate, and bromide. However, the most preferred counterion agent is triethylammonium acetate.

In yet a further aspect, the invention provides a method for storing a medium used for separating polynucleotides, e.g., the beads of a MIPC column or a monolith, in order to improve the resolution of double stranded DNA fragments separated using the medium. In the case of a MIPC column, the preferred method includes flowing a solution containing a multivalent cation binding agent through the column prior to storing the column. In a preferred embodiment, the multivalent cation binding agent is a coordination compound, examples of which include water-soluble chelating agents and crown ethers. Specific examples include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyidithiocarbarbamate, and zinc dibenzyldithiocarbamate. However, the most preferred chelating agent is EDTA. In this aspect of the invention, the solution preferably includes an organic solvent as exemplified by alcohols, nitriles, dimethylformamide, tetrahydrofuran, esters, and ethers. The most preferred organic solvent is acetonitrile. The solution can also include a counterion agent such as lower primary, secondary and tertiary amines, and lower trialkyammonium salts, or quaternary ammonium salts. More specifically, the counterion agent can be octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, tetrabutylammonium acetate, and mixtures of any one or more of the above. The counterion agent includes an anion, e.g., acetate, carbonate, bicarbonate, phosphate, sulfate, nitrate, propionate, formate, chloride, perchlorate, and bromide. However, the most preferred counterion agent is triethylammonium acetate.

BRIEF DESCRIPTION OF THE DRAWINGS

FIG. 1 is a schematic representation of how the DNA Separation Factor is applied to a separation.

FIG. 4 is a MIPC separation of pUC18 DNA-HaeIII digestion fragments on a column containing alkylated poly (styrene-divinylbenzene) beads. Peaks are labeled with the number of base pairs of the eluted fragment.

DETAILED DESCRIPTION OF THE INVENTION

Figure 2:
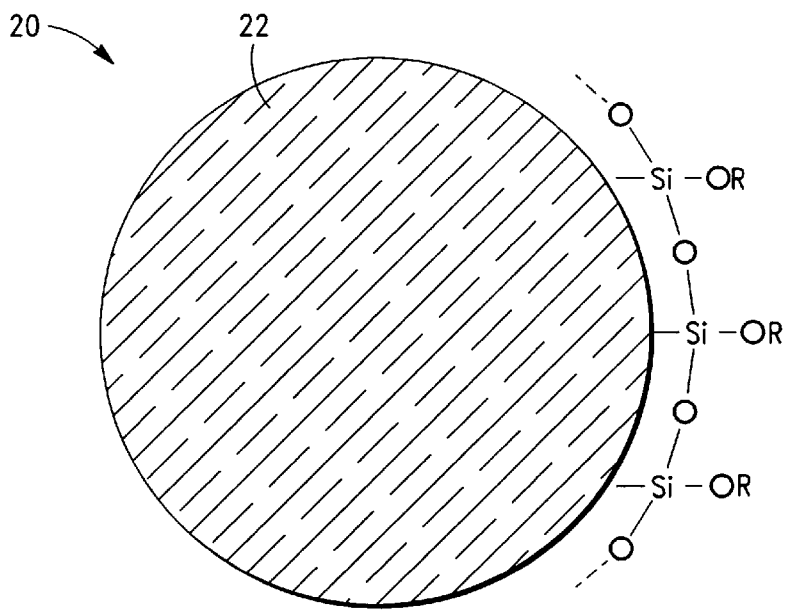
FIG. 2 is a schematic drawing of a cross-section of a representation of a reverse phase bead with a silica core which has been derivatized with a non-polar surface.
Figure 3:
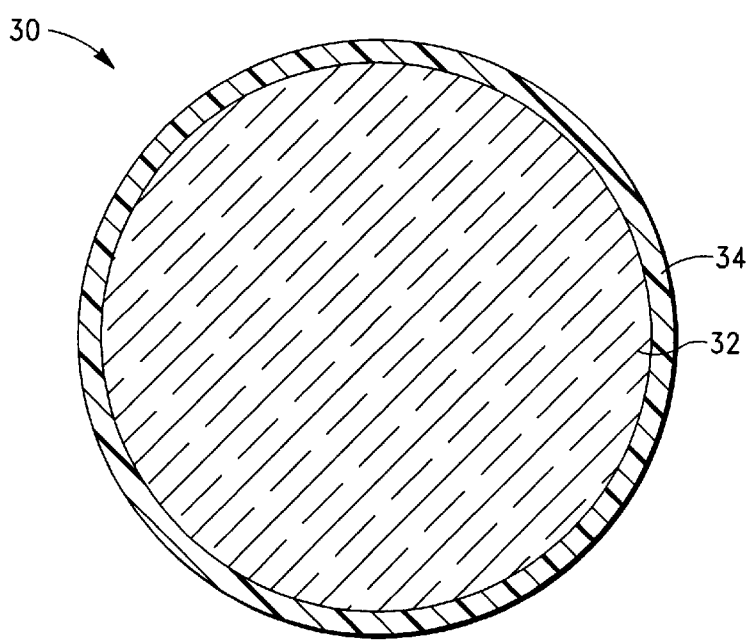
FIG. 3 is a schematic drawing of a cross-section of a representation of a reverse phase bead with a silica core and polymer shielding.

In its most general form, the subject matter of the present invention concerns the separation of polynucleotides. e.g. DNA, utilizing a stationary separation medium having non-polar surfaces. The preferred surfaces are essentially free from multivalent cation contamination which can trap polynucleotides. The separation is performed on the stationary phase surface. The surface can be porous, but preferably any surface pores are of a size which excludes the smallest polynucleotide being analyzed.

The medium can be enclosed in a column. In one embodiment, the non-polar surfaces comprise the surfaces of beads. In an alternative embodiment, the surfaces comprise the surfaces of interstitial spaces in a molded monolith. For purposes of simplifying the description of the invention and not by way of limitation, the separation of polynucleotides using nonporous beads, and the preparation of such beads, will be primarily described herein, it being understood that other separation surfaces, such as the interstitial surfaces of monoliths, are intended to be included within the scope of this invention. Monoliths such as derivatized silica gel rods contain separation media which have been formed inside a column as a unitary structure having through pores or interstitial spaces which allow eluting solvent and analyte to pass through and which provide the non-polar separation surface.

In general, the only requirement for the separation media of the present invention is that they must have a surface that is either intrinsically non-polar or be bonded with a material that forms a surface having sufficient non-polarity to interact with a counterion agent.

In one aspect, the subject matter of the present invention is the separation of polynucleotides by Matched Ion Polynucleotide Chromatography utilizing columns filled with nonporous beads having an average diameter of about 0.5–100 microns; preferably, 1–10 microns; more preferably, 1–5 microns. Beads having an average diameter of 1.0–3.0 microns are most preferred.

In U.S. Pat. No. 5,585,236, Bonn, et al., had characterized the polynucleotide separation process as reverse phase ion pairing chromatography (RPIPC). However, since RPIPC does not incorporate certain essential characteristics described in the present invention, another term, Matched Ion Polynucleotide Chromatography (MIPC), has been selected. MIPC as used herein, is defined as a process for separating single and double stranded polynucleotides using non-polar beads, wherein the process uses a counter ion agent, and an organic solvent to elute the polynucleotide from the beads, and wherein the beads are characterized as having a DNA Separation Factor of at least 0.05. In a preferred embodiment, the beads are characterized as having a DNA Separation Factor of at least 0.5.

The performance of the beads of the present invention is demonstrated by high efficiency separation by MIPC of double stranded and single stranded DNA. Applicants have found that the best criterion for measuring performance of the beads is a DNA Separation Factor. This is measured as the resolution of 257- and 267-base pair double stranded DNA fragments of a pUC18 DNA-HaeII restriction digest and is defined as the ratio of the distance from the valley between the peaks to the top of the peaks, over the distance from the baseline to the top of the peaks. Referring to the schematic representation of FIG. 1, the DNA Separation Factor is determined by measuring the distance "a" from the baseline to the valley "e" between the peaks "b" and "c" and the distance "d" from the valley "e" to the top of one of the peaks "b" or "c". If the peak heights are unequal, the highest peak is used to obtain "d." The DNA Separation Factor is the ratio of d/(a+d). The peaks of 257- and 267-base pairs in this schematic representation are similar in height. Operational beads of the present invention have a DNA Separation Factor of at least 0.05. Preferred beads have a DNA Separation Factor of at least 0.5. In an optimal embodiment, the beads have a DNA Separation Factor of at least 0.95.

Without wishing to be bound by theory, Applicants believe that the beads which conform to the DNA Separation Factor as specified herein have a pore size which essentially excludes the polynucleotides being separated from entering the bead. As used herein, the term "nonporous" is defined to denote a bead which has surface pores having a diameter that is less than the size and shape of the smallest DNA fragment in the separation in the solvent medium used therein. Included in this definition are beads having these specified maximum size restrictions in their natural state or which have been treated to reduce their pore size to meet the maximum effective pore size required. Preferably, all beads which provide a DNA Separation Factor of at least 0.05 are intended to be included within the definition of "nonporous" beads.

The surface conformations of nonporous beads of the present invention can include depressions and shallow pit-like structures which do not interfere with the separation process. A pretreatment of a porous bead to render it nonporous can be effected with any material which will fill the pores in the bead structure and which does not significantly interfere with the MIPC process.

Pores are open structures through which mobile phase and other materials can enter the bead structure. Pores are often interconnected so that fluid entering one pore can exit from another pore. Applicants believe that pores having dimensions that allow movement of the polynucleotide into the interconnected pore structure and into the bead impair the resolution of separations or result in separations that have very long retention times. In MIPC, however, the beads are "nonporous" and the polynucleotides do not enter the bead structure.

The term polynucleotide is defined as a linear polymer containing an indefinite number of nucleotides, linked from one ribose (or deoxyribose) to another via phosphoric residues. The present invention can be used in the separation of RNA or of double- or single-stranded DNA. For purposes of simplifying the description of the invention, and not by way of limitation, the separation of double-stranded DNA will be described in the examples herein, it being understood that all polynucleotides are intended to be included within the scope of this invention.

Chromatographic efficiency of the column beads is predominantly influenced by the properties of surface and near-surface areas. For this reason, the following descriptions are related specifically to the close-to-the-surface region of the beads. The main body and/or the center of such beads can exhibit entirely different chemistries and sets of physical properties from those observed at or near the surface of the beads of the present invention.

In another embodiment of the present invention, the separation medium can be in the form of a monolith such as a rod-like monolithic column. The monolithic column can be polymerized or formed as a single unit inside of a tube. The through pore or interstitial spaces provide for the passage of eluting solvent and analyte materials. The separation is performed on the stationary surface. The surface can be porous, but is preferably nonporous. The form and function of the separations are identical to columns packed with beads. As with beads, the pores contained in the rod must be compatible with DNA and not trap the material. Also, the rod must not contain contamination that will trap DNA.

In one embodiment of the present invention, the separation medium is continuous monolithic silica gel. A molded monolith can be prepared by polymerization within the confines of a chromatographic column (e.g., to form a rod) or other containment system. A monolith is preferably obtained by the hydrolysis and polycondensation of alkoxysilanes. A preferred monolith is derivatized in order to produce non-polar interstitial surfaces. Chemical modification of silica monoliths with ocatdecyl, methyl or other ligands can be carried out. An example of a preferred derivatized monolith is one which is polyfunctionally derivatized with octadecylsilyl groups. The preparation of derivatized silica monoliths is by conventional methods well known in the art as described in Example 15 and in the following references which are hereby incorporated in their entirety herein: Nakanishi, et al., *J. Sol-Gel Sci. Technol.* 8:547 (1997); Nakanishi, et al., *Bull, Chem. Soc. Jpn.* 67:1327 (1994); Cabrera, et al., *Trends Analytical Chem.* 17:50 (1998); Jinno, et al., *Chromatographia* 27:288 (1989).

The beads of the invention comprise a nonporous particle which has non-polar molecules or a non-polar polymer attached to or coated on its surface. In general, the beads comprise nonporous particles which have been coated with a polymer or which have substantially all surface substrate groups reacted with a non-polar hydrocarbon or substituted hydrocarbon group, and any remaining surface substrate groups endcapped with a tri(lower alkyl)chlorosilane or tetra(lower alkyl)dichlorodisilazane as described above.

The nonporous particle is preferably an inorganic particle, but can be a nonporous organic particle. The nonporous particle can be, for example, silica, silica carbide, silica nitrite, titanium oxide, aluminum oxide, zirconium oxide, carbon, insoluble polysaccharides such as cellulose, or diatomaceous earth, or any of these materials which have been modified to be nonporous. Examples of carbon particles include diamond and graphite which have been treated to remove any interfering contaminants. The preferred particles are essentially non-deformable and can withstand high pressures. The nonporous particle is prepared by known procedures. The preferred particle size is about 0.5–100 microns; preferably, 1–10 microns; more preferably, 1–5 microns. Beads having an average diameter of 1.0–3.0 microns are most preferred.

Because the chemistry of preparing conventional silica-based reverse phase HPLC materials is well-known, most of the description of the beads of the invention herein is presented in reference to silica. It is to be understood, however, that other nonporous particles, such as those listed above, can be modified in the same manner and substituted for silica in the process of the invention. For a description of the general chemistry of silica, see Poole, Colin F. and Salwa K. Poole, *Chromatography Today,* Elsevier:New York (1991), pp. 313–342 and Snyder, R. L. and J. J. Kirkland, *Introduction to Modern Liquid Chromatography,* $2^{nd}$ ed., John Wiley & Sons, Inc.:New York (1979), pp. 272–278, the disclosures of which are hereby incorporated herein by reference in their entireties.

The nonporous beads of the invention are characterized by having minimum exposed silanol groups after reaction with the coating or silating reagents. Minimum silanol groups are needed to reduce the interaction of the DNA with the substrate and also to improve the stability of the material in a high pH and aqueous environment. Silanol groups can be harmful because they can repel the negative charge of the DNA molecule, preventing or limiting the interaction of the DNA with the stationary phase of the column. Another possible mechanism of interaction is that the silanol can act as ion exchange sites, taking up metals such as iron (III) or chromium (III). Iron (III) or other metals which are trapped on the column can distort the DNA peaks or even prevent DNA from being eluted from the column.

Silanol groups can be hydrolyzed by the aqueous-based mobile phase. Hydrolysis will increase the polarity and reactivity of the stationary phase by exposing more silanol sites, or by exposing metals that can be present in the silica core. Hydrolysis will be more prevalent with increased underivatized silanol groups. The effect of silanol groups on the DNA separation depends on which mechanism of interference is most prevalent. For example, iron (III) can become attached to the exposed silanol sites, depending on whether the iron (III) is present in the eluent, instrument or sample.

The effect of metals can only occur if metals are already present within the system or reagents. Metals present within the system or reagents can get trapped by ion exchange sites on the silica. However, if no metals are present within the system or reagents, then the silanol groups themselves can cause interference with DNA separations. Hydrolysis of the exposed silanol sites by the aqueous environment can expose metals that might be present in the silica core.

Fully hydrolyzed silica contains a concentration of about 8 μmoles of silanol groups per square meter of surface. At best, because of steric considerations, a maximum of about 4.5 μmoles of silanol groups per square meter can be reacted, the remainder of the silanol being sterically shielded by the reacted groups. Minimum silanol groups is defined as reaching the theoretical limit of or having sufficient shield to prevent silanol groups from interfering with the separation.

Numerous methods exist for forming nonporous silica core particles. For example, sodium silicate solution poured into methanol will produce a suspension of finely divided spherical particles of sodium silicate. These particles are neutralized by reaction with acid. In this way, globular particles of silica gel are obtained having a diameter of about 1–2 microns. Silica can be precipitated from organic liquids or from a vapor. At high temperature (about 2000° C.), silica is vaporized, and the vapors can be condensed to form finely divided silica either by a reduction in temperature or by using an oxidizing gas. The synthesis and properties of silica are described by R. K. Iler in *The Chemistry of Silica, Solubility, Polymerization, Colloid and Surface Properties, and Biochemistry*, John Wiley & Sons:New York (1979).

W. Stöber et al. described controlled growth of monodisperse silica spheres in the micron size range in *J. Colloid and Interface Sci.*, 26:62–69 (1968). Stöber et al. describe a system of chemical reactions which permit the controlled growth of spherical silica particles of uniform size by means of hydrolysis of alkyl silicates and subsequent condensation of silicic acid in alcoholic solutions. Ammonia is used as a morphological catalyst. Particle sizes obtained in suspension range from less than 0.05 μm to 2 μm in diameter.

Nonporous silica core beads can be obtained from Micra Scientific (Northbrook, Ill.) and from Chemie Uetikkon (Lausanne, Switzerland).

To prepare the nonporous beads of the invention, the nonporous particle is coated with a polymer or reacted and endcapped so that substantially all surface substrate groups of the nonporous particle are blocked with a non-polar hydrocarbon or substituted hydrocarbon group. This can be accomplished by several methods.

The organic bonded-phase siloxane coating can be made as a monomolecular layer or as a polymerized multilayer coating. Packings with so-called monomolecular organic layers are normally prepared by reacting the surface silanol groups of siliceous-base particles with mono-, di-, or trifunctional chloro-, dimethyl-, amino-, siloxy-, or alkoxy-silanes. Typical monofunctional reactants used in these reactions include X—Si—R, where X=Cl, OH, $OCH_3$, or $OC_2H_5$, and R is an organic radical. FIG. 2 is a schematic representation of a bead 20 having a silica core 22 and a monomolecular organic layer. (The figure does not necessarily reflect the morphology or pore structure of the beads of the invention and is meant for illustrative purposes only.)

Using bi- and trifunctional reactants, such as $R_2SiX_2$ and $RSiX_3$, for the surface modifications, up to two Si—X groups per bonded functional group remain unreacted. After treatment with water, hydrolysis of these unreacted groups takes place, and additional silanol groups are formed (sometimes in a polymer matrix) in about the same concentration as the bonded organic functional groups present in the packing. These acidic organo-silanol groups can significantly affect the retention behavior of solutes and adversely influence the stability of the packing in aqueous solutions at pH>7.

Thus, incomplete reaction of the surface with the silane reagent, or the formation of new Si—OH groups from using bi- or trifunctional modifiers, can result in a population of residual acidic Si—OH groups that are readily accessible to molecules of the mobile phase or sample. Therefore, the recent trend is toward (a) a dense monolayer of functional groups instead of partial coverage and (b) the use of monofunctional dimethylsilanes [X—Si$(CH_3)_2$—R] to provide a homogeneous organic coating with a minimum possibility of residual Si—OH groups. Monochlorosilane reagents are preferred, if the required organic functionality can be prepared. If two of the R groups in the monofunctional modifier are methyl, surface coverage can be as high as about 4 μmoles per square meter of organic (based on carbon analysis). In the latter case, residual Si—OH groups on the silica surface are unavailable for chromatographic interactions with most solutes because of steric shielding.

The reaction of organosilanols (e.g., HO—Si—$R_3$) or organoalkoxy- (e.g., RO—Si—$R_3$) silanes with silica supports without polymerization can also produce good packings. These reactions are relatively reproducible, provided that traces of water or other reactive species are absent. Unreacted, accessible silanols can be left after the initial reaction, but these can be removed by capping of the packing with chlorotrimethylsilane (providing the R groups do not react with the latter silane).

According to one method, the nonporous particle is coated with a polymer coating. Suitable polymers for use in coating the particle include chain reaction polymers and step reaction polymers, for example, polystyrene, polymethacrylate, polyethylene, polyurethane, polypropylene, polyamide, insoluble polysaccharides such as cellulose, polydimethyl siloxane, polydialkyl siloxane, and related materials. The polymer coating can be attached to the nonporous particle by means of a multi-coating process so that complete shielding of the surface is achieved.

Figure 21:
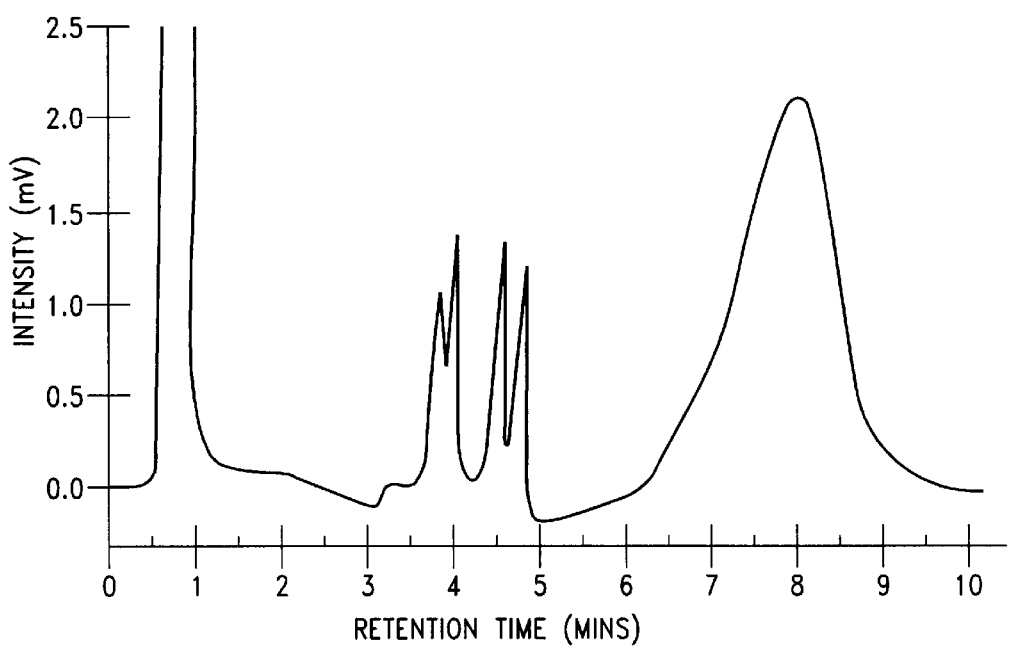
FIG. 21 is an elution profile of another injection of the same 209 bp mixture and using the same column as in FIG. 20, but after changing the guard cartridge and replacing the pump-valve filter.

In the last few years, new bonded phase packings, known as polymer-coated or polymer-encapsulated packings, have been introduced based on techniques used to prepare immobilized stationary phases for open tubular column gas chromatography. In this case, the phases are prepared by mechanically coating either bare silica or presilanized silica microparticles with a poly(siloxane) or poly(butadiene) prepolymer, which is then immobilized by peroxide, azo-tert-butane, or gamma radiation-induced chemical crosslinking reactions. FIG. 21 is a schematic illustration of a coated bead 30 having a silica core 32 and polymer coating 34. (The figure does not necessarily reflect the morphology or pore structure of the beads of the invention and is meant for illustrative purposes only.)

An alternative method comprises a combination of covalent bonding with a vinyl-containing silane molecule and then polymerizing a coating on the surface of the particles. A second coating can be applied if residual silanol groups or metal groups are present.

In a variation of this method, the silica surface is first modified by reaction with vinyltrichlorosilane, followed by polymerizing acrylic acid derivatives to and over the derivatized silica surface. The availability of a large number of useful monomers and prepolymers has enabled a wide variety of reverse phase, polar, and ion exchange packings to be prepared using the same general reaction. Also, since the general approach does not depend on the chemistry of the underlying substrate, materials other than silica, for example, alumina and zirconia, can be modified and used under conditions for which silica is unsuitable, for example, with mobile phases outside the pH range 2–7.5. Returning to silica, presilanization decreases the number of active silanol groups, which are then further shielded by the polymeric film anchored over the surface. In reverse phase liquid chromatography, these packings have shown improved chromatographic properties compared to monomeric, chemically bonded phases for the separation of basic solutes. Polymer-encapsulated packings have a film thickness of about 1 nm to maintain reasonable mass transfer characteristics. A description of this procedure has been published by H. Engelhart et al. (*Chromatographia*, 27:535 (1989)).

The polymer-coated beads prepared according to either of the above methods can be used in their unmodified state or can be modified by substitution with a hydrocarbon group. Any hydrocarbon group is suitable. The term "hydrocarbon" as used herein is defined to include alkyl and alkyl substituted aryl groups, having from 1 to 1,000,000 carbons, the alkyl groups including straight chained, branch chained, cyclic, saturated, unsaturated nonionic functional groups of various types including, aldehyde, ketone, ester, ether, alkyl groups, and the like, and the aryl groups including as monocyclic, bicyclic, and tricyclic aromatic hydrocarbon groups including phenyl, naphthyl, and the like. Methods for hydrocarbon substitution are conventional and well-known in the art and are not an aspect of this invention. The hydrocarbon can also contain hydroxy, cyano, nitro groups, or the like which are considered to be non-polar, reverse phase functional groups. The preferred hydrocarbon groups are alkyl groups, and the description of suitable substitution processes hereinbelow are presented as alkylation for purposes of simplification and not by way of limitation, it being understood that aryl substitution by conventional procedures are also intended to be included within the scope of this invention.

The polymer-coated beads can be alkylated by reaction with the corresponding alkyl halide such as the alkyl iodide. Alkylation is achieved by mixing the polymer-coated beads with an alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. Substitution with hydrocarbon groups having from 1 to 1,000,000 and preferably from 1 to 22 carbons can be effected by these processes. Hydrocarbon groups having from 23 to 1,000,000 carbons are referenced herein as hydrocarbon polymers.

Alkylation can be accomplished by a number of known synthesis procedures. These include Friedel-Crafts alkylation with an alkyl halide, attachment of an alkyl alcohol to a chloromethylated bead to form an ether, etc. Although the preferred method for alkylating the polymer-coated beads of the present invention is alkylation after the polymer coating has been formed on the nonporous particle, an alternative method of alkylation is to polymerize alkylated monomers to form an alkylated polymer coating on the nonporous particle. In this embodiment, the monomers will be substituted with alkyl groups having any number of carbon atoms, for example, from 1 to 100, 1 to 50 or 1 to 24, for example, depending upon the requirements of the separation variables.

As an alternative to polymer coating, the nonporous particle can be functionalized with an alkyl group or other non-polar functional group including cyano, ester, and other non-ionic groups, followed by a complete endcapping process to reduce silanol and metal interaction. Endcapping of the nonporous particle can be achieved by reacting the particle with trialkyl chlorosilane or tetraalkyl dichlorodisilazane, such as, for example, trimethyl chlorosilane or dichloro-tetraisopropyl-disilazane.

A large number of factors influence the success of the bonding reactions and the quality of the final bonded-phase product. The rate and extent of the bonding reaction depends on the reactivity of the silane, choice of solvent and catalyst, time, temperature, and the ratio of reagents to substrate. Reactive organosilanes with Cl, OH, OR, $N(CH_3)_2$, $OCOCF_3$, and enolates as leaving groups have been widely used. The dimethylamine, trifluoroacetate, and enol ethers of pentane-2,4-dione are the most reactive leaving groups, although economy, availability, and familiarity result in the chlorosilanes and alkoxysilanes being the most widely used, particularly among commercial manufacturers. Initially, reactions can be almost stoichiometric but, as the surface coverage approaches a maximum value, the reaction becomes very slow. For this reason, reaction times tend to be long (12–72 hours), reaction temperatures moderately high (in most cases, around 100° C.) and, in the case of chlorosilanes, an acid acceptor catalyst (e.g., pyridine) is used. Some reagents, such as the alkylsilyl enolates and alkylsilyldimethylamines, do not require additional catalyst, or even solvent, to carry out the reaction. The most common solvents employed are toluene and xylene, although other solvents, such as carbon tetrachloride, trichloroethane, and dimethylformamide (DMF), have been recommended as being superior. Since the bonding reactions are carried out by refluxing in an inert atmosphere, solvents are often selected based on their capacity to be a good solvent for the organosilanes and to attain the desired reaction temperature at reflux. Except for 3-cyanopropylsiloxane bonded phases, the high reactivity of chlorosilanes towards certain polar functional groups (e.g., OH, etc.) precludes the use of these groups for the preparation of polar, reverse phase bonded phases. Alkoxysilanes containing acidic or basic functional groups are autocatalytic and the bonded phases are usually prepared by refluxing the silane in an inert solvent at a temperature high enough to distill off the alcohol formed by the condensation reaction with the surface silanol groups. Bonding of neutral, polar ligands generally requires the addition of a catalyst, such as toluene-4-sulfonic acid or triethylamine, in the presence of sufficient water to generate monolayer coverage of the silica. The presence of water speeds up the hydrolysis of the alkoxy groups of the adsorbed organosilane, which tends to react with surface silanol groups rather than polymerize in solution. It seems to be a general problem in the preparation of polar bonded phases that surface silanol groups are blocked by physically adsorbed organosilanes, giving rise to a lower bonded phase density after workup than the maximum theoretically predicted. The bonded phase density can be increased by repeating the reaction a second time or exposed silanol groups minimized by endcapping.

Although most bonded phases are prepared from organosilanes containing a single functionalized ligand bonded to silicon, with the remaining groups being leaving groups and/or methyl groups, more highly substituted organosilanes can also be used. Bifunctional organosilanes, such as 1,3-dichlorotetraisopropyldisilazane, are able to react with surface silanol groups at both ends of the chain, forming a bonded phase that is more hydrolytically stable than bonded phases formed from conventional organosilanes. The bidentate organosilanes have reactive sites that more closely match the spacing of the silanol groups on the silica surface and provide a higher bonded phase coverage than is achieved with dichlorosilanes with both leaving groups attached to the same silicon atom. For alkyldimethylsilanes, increasing the length of the alkyl group increases the hydrolytic stability of the bonded phase relative to that of the trimethylsilyl bonded ligands. Increasing the chain length of the methyl groups increases the hydrolytic stability of the bonded phase, but reduces the phase coverage due to steric effects. The use of monofunctional organosilanes containing one or two bulky groups, for example, isopropyl or t-butyl, on the silicon atom of the silane can become more important in the preparation of bonded phases for use at low pH. The bulky alkyl groups provide better steric protection to the hydrolytically sensitive siloxane groups on the packing surface than does the methyl group.

The general process of coating and endcapping of a silica substrate is well-known technology. However, the general understanding of those who have used these materials is they are not suitable for high performance double stranded DNA separations. However, the beads of this invention are formed by a more careful application of the coating and end-capping procedures to effect a thorough shielding of the silica core, the resulting beads having the ability to perform rapid separations of both single stranded and double stranded DNA which are equal to or better than those achieved using the alkylated nonporous polymer beads disclosed in U.S. Pat. No. 5,585,236, for example.

Care must be taken during the preparation of the beads to ensure that the surface of the beads has minimum silanol or metal oxide exposure and that the surface remains nonporous.

In an important aspect of the present invention, the beads or other media of the invention are characterized by having low amounts of metal contaminants or other contaminants that can bind DNA. The preferred beads are characterized by having been subjected to precautions during production, including a decontamination treatment, such as an acid wash treatment, designed to substantially eliminate any multivalent cation contaminants (e g. Fe(III), Cr(III), or colloidal metal contaminants). Only very pure, non-metal containing materials should be used in the production of the beads in order that the resulting beads will have minimum metal content.

In addition to the beads themselves being substantially metal-free, Applicants have also found that, to achieve optimum peak separation during RPIPC, the separation column and all process solutions held within the column or flowing through the column are preferably substantially free of multivalent cation contaminants (e.g. Fe(III), Cr(III), and colloidal metal contaminants). As described in commonly owned U.S. Pat. No. 5,772,889 to Gjerde (1998), and in commonly owned, co-pending U.S. patent applications Ser. No. 09/081,040 filed May 18, 1998 and Ser No. 09/080,547 filed May 18, 1998, all three of which are incorporated by reference herein, this can be achieved by supplying and feeding solutions that enter the separation column with components which have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, passivated stainless steel, and organic polymer. Metals found in stainless steel, for example, do not harm the separation, unless they are in an oxidized or colloidal partially oxidized state. For example, 316 stainless steel frits are acceptable in column hardware, but surface oxidized stainless steel frits harm the DNA separation.

For additional protection, multivalent cations in mobile phase solutions and sample solutions entering the column can be removed by contacting these solutions with multivalent cation capture resin before the solutions enter the column to protect the separation medium from multivalent cation contamination. The multivalent capture resin is preferably cation exchange resin and/or chelating resin.

Mixtures of polynucleotides in general, and o,uble stranded DNA in particular, are effectively separated using Matched Ion Polynucleotide Chromatography (MIPC). MIPC separations of polynucleotides at non-denaturing temperature, typically less than about 50° C., are based on base pair length. However, even traces of multivalent cations anywhere in the solvent flow path can cause a significant deterioration in the resolution of the separation after multiple uses of an MIPC column. This can result in increased cost caused by the need to purchase replacement columns and increased downtime.

Therefore, effective measures are preferably taken to prevent multivalent metal cation contamination of the separation system components, including separation media and mobile phase contacting. These measures include, but are not limited to, washing protocols to remove traces of multivalent cations from the separation media and installation of guard cartridges containing cation capture resins, in line between the mobile phase reservoir and the MIPC column. These, and similar measures, taken to prevent system contamination with multivalent cations have resulted in extended column life and reduced analysis downtime.

There are two places where multivalent cation binding agents, e.g., chelators, are used in MIPC separations. In one embodiment, these binding agents can be incorporated into a solid through which the mobile phase passes. Contaminants are trapped before they reach places within the system that can harm the separation. In these cases, the functional group is attached to a solid matrix or resin (e.g., a flow-through cartridge, usually an organic polymer, but sometimes silica or other material). The capacity of the matrix is preferably about 2 meq/g. An example of a suitable chelating resin is available under the trademark CHELEX 100 (Dow Chemical Co.) containing an iminodiacetate functional group.

In another embodiment, the multivalent cation binding agent can be added to the mobile phase. The binding functional group is incorporated into an organic chemical structure. The preferred multivalent cation binding agent fulfills three requirements. First, it is soluble in the mobile phase. Second, the complex with the metal is soluble in the mobile phase. Multivalent cation binding agents such as EDTA fulfill this requirement because both the chelator and the multivalent cation binding agent-metal complex contain charges which make them both water-soluble. Also, neither precipitate when acetonitrile, for example, is added. The solubility in aqueous mobile phase can be enhanced by attaching covalently bound ionic functionality, such as, sulfate, carboxylate, or hydroxy. A preferred multivalent cation binding agent can be easily removed from the column by washing with water, organic solvent or mobile phase. Third, the binding agent must not interfere with the chromatographic process.

The multivalent cation binding agent can be a coordination compound. Examples of preferred coordination compounds include water soluble chelating agents and crown ethers. Non-limiting examples of multivalent cation binding agents which can be used in the present invention include acetylacetone, alizarin, aluminon, chloranilic acid, kojic acid, morin, rhodizonic acid, thionalide, thiourea, α-furildioxime, nioxime, salicylaldoxime, dimethylglyoxiiiie, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate.

These and other examples are described by Perrin in *Organic Complexing Reagents: Structure, Behavior, and Application to Inorganic Analysis,* Robert E. Krieger Publishing Co. (1964). In the present invention, a preferred multivalent cation binding agent is EDTA.

To achieve high resolution chromatographic separations of polynucleotides, it is generally necessary to tightly pack the chromatographic column with the solid phase nonporous beads. Any known method of packing the column with a column packing material can be used in the present invention to obtain adequate high resolution separations. Typically, a slurry of the beads is prepared using a solvent having a density equal to or less than the density of the beads. The column is then filled with the bead slurry and vibrated or agitated to improve the packing density of the beads in the column. Mechanical vibration or sonification are typically used to improve packing density.

For example, to pack a 50×4.6 mm i.d. column, 2.0 grams of beads can be suspended in 10 mL of methanol with the aid of sonification. The suspension is then packed into the column using 50 mL of methanol at 8,000 psi of pressure. This improves the density of the packed bed.

The separation method of the invention is generally applicable to the chromatographic separation of single stranded and double stranded polynucleotides of DNA and RNA. Samples containing mixtures of polynucleotides can result from total synthesis of polynucleotides, cleavage of DNA or RNA with restriction endonucleases or with other enzymes or chemicals, as well as polynucleotide samples which have been multiplied and amplified using polymerase chain reaction techniques.

The method of the present invention can be used to separate double stranded polynucleotides having up to about 1500 to 2000 base pairs. In many cases, the method is used to separate polynucleotides having up to 600 bases or base pairs, or which have up to 5 to 80 bases or base pairs.

In a preferred embodiment, the separation is by MIPC. The nonporous beads of the invention are used as a reverse phase material that will function with counter ion agents and a solvent gradient to effect the DNA separations. In MIPC, the DNA fragments are matched with a counterion agent and then subjected to reverse phase chromatography using the nonporous beads of the present invention.

There are several types of counterions suitable for use with MIPC. These include a mono-, di-, or trialkylamine that can be protonated to form a positive counter charge or a quaternary alkyl substituted amine that already ontains a positive counter charge. The alkyl substitutions may be uniform (for example, triethylammonium acetate or tetrapropylammonium acetate) or mixed (for example, propyldiethylammonium acetate). The size of the alkyl group may be small (methyl) or large (up to 30 carbons) especially if only one of the substituted alkyl groups is large and the others are small. For example octyldimethylammonium acetate is a suitable counterion agent. Preferred counterion agents are those containing alkyl groups from the ethyl, propyl or butyl size range.

The purpose of the alkyl group is to impart a nonpolar character to the polynucleic acid through a matched ion process so that the polynucleic acid can interact with the nonpolar surface of the separation media. The requirements for the extent of nonpolarity of the counterion-DNA pair depends on the polarity of the separation media, the solvent conditions required for separation, and the particular size and type of fragment being separated. For example, if the polarity of the separation media is increased, then the polarity of the counterion agent may have to change to match the polarity of the surface and increase interaction of the counterion-DNA pair. Triethylammonium acetate is preferred although quaternary ammonium reagents such as tetrapropyl or tetrabutyl ammonium salts can be used when extra nonpolar character is needed or desired. In general, as the polarity of the alkyl group is increased, size specific separations, sequence independent separations become more possible. Quaternary counterion reagents are not volatile, making collection of fragments more difficult.

The mobile phase preferably contains a counterion agent. Typical counterion agents include trialkylammonium salts of organic or inorganic acids, such as lower alkyl primary, secondary, and lower tertiary amines, lower trialkyammonium salts and lower quaternary alkyalmmonium salts. Lower alkyl refers to an alkyl radical of one to six carbon atoms, as exemplified by methyl, ethyl, n-butyl, i-butyl, t-butyl, isoamyl, n-pentyl, and isopentyl. Examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methyihexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, and tributylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde, et al. in *Ion Chromatography,* 2nd Ed., Dr. Alfred H üthig Verlag Heidelberg (1987). Counterion agents that are volatile are preferred for use in the method of the invention, with triethylammonium acetate (TEAA) and triethylammonium hexafluoroisopropyl alcohol being most preferred.

To achieve optimum peak resolution during tne separation of DNA by MIPC using the beads of the invention, the method is performed at a temperature within the range of 20° C. to 90° C. to yield a back-pressure not greater than 10,000 psi. In general, separation of single-stranded fragments should be performed at higher temperatures.

Applicants have found that the temperature at which the separation is performed affects the choice of organic solvents used in the separation. When the separation is performed at a temperature within the above range, an organic solvent that is water soluble is preferably used, for example, alcohols, nitriles, dimethylformamide (DMF), esters, and ethers. Water soluble solvents are defined as those which exist as a single phase with aqueous systems under all conditions of operation of the present invention. Solvents which are particularly preferred for use in the method of this invention include methanol, ethanol, 1-propanol, 2-propanol, tetrahydrofuran (THF), and acetonitrile, with acetonitrile being most preferred. In some cases, it may be desired to increase the range of concentration of organic solvent used to perform the separation. For example, increasing the alkyl length on the counterion agent will increase the nonpolarity of the counterion-DNA pair resulting in the need to either increase the concentration of the mobile phase organic solvent, or increase the strength of the organic solvent type, e.g. acetonitrile is about two times more effective than methanol for eluting polynucleic acids. There is a positive correlation between concentration of the organic solvent required to elute a fragment from the column and the length of the fragment. However, at high organic solvent concentrations, the polynucleotide could precipitate. To avoid precipitation, a strong organic solvent or a smaller counterion alkyl group can be used. The alkyl group on the counterion reagent can also be substituted with halides, nitro groups, or the like to moderate polarity.

Applicants have determined that the chromatographic separations of double stranded DNA fragments exhibit unique Sorption Enthalpies ($AH_{50}p$. Two compounds (in this case, DNA fragments of different size) can only be separated if they have different partition coefficients (K). The Nernst partition coefficient is defined as the concentration of an analyte (A) in the stationary phase divided by its concentration in the mobile phase:

$$K = \frac{[A]_s}{[A]_m}$$

The partition coefficient (K) and the retention factor (k) are related through the following equations:

$$K = \frac{n(A)_s V_m}{n(A)_m V_s} \text{ and } k = \frac{n(A)_s}{n(A)_m}$$

the quotient $V_m/V_s$ is also called phase volume ratio ($\Phi$). Therefore:

$$k = K\Phi$$

To calculate the sorption enthalpies, the following fundamental thermodynamic equations are necessary:

$$\ln K = -\frac{\Delta G}{RT}, \ln k = -\frac{\Delta G_{sorp}}{RT} + \ln \Phi \text{ and } \Delta G_{sorp} = \Delta H_{sorp} - T\Delta S_{sorp}$$

By transforming the last two equations, on e obtains the Van't Hoff equation:

$$\ln k = -\frac{\Delta H_{sorp}}{RT} + \frac{\Delta S_{sorp}}{R} + \ln \Phi$$

From a plot In k versus 1/T, the sorption enthalpy $\Delta H_{sorp}$ can be obtained from the slope of the graph (if a straight line is obtained). $\Delta S_{sorp}$ can be calculated if the phase volume ratio ($\Phi$) is known.

Experiments on polymeric beads coated with poly (styrene-divinylbenzene) also give a negative slope for a plot of In k versus 1/T, although the plot is slightly curved.

If the acetonitrile is replaced with methanol, the retention factor k decreases with increasing temperature, indicating the retention mechanism is an exothermic process ($\Delta H_{sorp} < 0$).

The thermodynamic data (as shown in the Examples hereinbelow) reflect the relative affinity of the DNA-counter ion agent complex for the beads of the invention and the elution solvent. An endothermic plot indicates a preference of the DNA complex for the bead. An exothermic plot indicates a preference of the DNA complex for the solvent over the bead. The plots shown herein are for alkylated and non-alkylated surfaces as described in the Examples. Most liquid chromatographic separations show exothermic plots.

Recently, MIPC has been successfully applied to the detection of mutations in double stranded DNA by separating heteroduplexes from homoduplexes as described in co-pending U.S. patent application Ser. No. 09/129,105 filed Aug. 4, 1998 which is herein incorporated by reference. Such separations depend on the lower temperature required to denature a heteroduplex at the site of base pair mismatch compared to a fully complimentary homoduplex DNA fragment. MIPC, when performed at a temperature wnich is sufficient to partially denature a heteroduplex is referred to herein as Denaturing Matched Ion Polynucleotide Chromatography (DMIPC). DMIPC is typically performed at a temperature between 52° C and 70° C. The optimum temperature for performing DMIPC is 54° C. to 59° C.

The precautions described hereinabove taken to remove multivalent metal cations were adequate for maintaining column life, as demonstrated by good separation efficiency, under non-denaturing conditions. However, Applicants have surprisingly found that when performed at partially denaturing temperature, conditions for effective DMIPC separations become more stringent. For example, a separation of a standard pUC18 HaeIII digest on a MIPC column at 50° C. provided a good separation of all the DNA fragments in the digest. However, a standard 209 bp DYS271 mutation detection mixture of homoduplexes and heteroduplexes, prepared as described in Example 15, applied to the same MIPC column and eluted under DMIPC conditions, i.e., 56° C., afforded a poor separation of the mixture components. In order to optimize column life and maintain effective separation performance of homoduplexes from heteroduplexes at partially denaturing temperatures, as is required for mutation detection, special column washing and storage procedures are used in the embodiments of the invention as described hereinbelow.

In one aspect of this invention, therefore, an aqueous solution of multivalent cation binding agent is flowed through the column to maintain separation efficiency. In order to maintain the separation efficiency of a MIPC column, the column is preferably washed with multivalent cation binding agent solution after about 500 uses or when the performance starts to degrade. Examples of suitable cation binding agents are as described hereinabove.

The concentration of a solution of the cation binding agent can be between 0.01 M and 1 M. In a preferred embodiment, the column washing solution contains EDTA at a concentration of about 0.03 to 0.1 M.

In another embodiment, the solution contains an organic solvent selected from the group consisting of acetonitrile, ethanol, methanol, 2-propanol, and ethyl acetate. A preferred solution contains at least 2% organic solvent to prevent microbial growth. In a most preferred embodiment a solution containing 25% acetonitrile is used to wash a MIPC column. The multivalent cation binding solution can contain a counterion agent as described hereinabove.

In one embodiment of a column washing procedure, the MIPC separation column is washed with the multivalent cation binding solution at an elevated temperature in the range of 50° C. to 80° C. In a preferred embodiment the column is washed with a solution containing EDTA, TEAA, and acetonitrile, in the 70° C. to 80° C. temperature range. In a specific embodiment, the solution contains 0.032 M EDTA, 0.1M TEAA, and 25% acetonitrile.

Column washing can range from 30 seconds to one hour. For example, in a high throughput DMIPC assay, the column can be washed for 30 seconds after each sample, followed by equilibration with mobile phase. Since DMIPC can be automated by computer, the column washing procedure can be incorporated into the mobile phase selection program without dditional operator involvement. In a preferred procedure, the column is washed with multivalent cation binding agent for 30 to 60 minutes at a flow rate preferably in the range of about 0.05 to 1.0 mL/min.

In one embodiment, a MIPC column is tested with a standard mutation detection mixture of homoduplexes and heteroduplexes after about 1000 sample analyses. If the separation of the standard mixture has deteriorated compared to a freshly washed column, then the column can be washed for 30 to 60 minutes with the multivalent cation binding solution at a temperature above about 50° C. to restore separation performance.

Applicants have found that other treatments for washing a column can also be used alone or in combination with those indicated hereinabove. These include: use of high pH washing solutions (e.g., pH 10–12), use of denaturants such as urea or formamide, and reverse flushing the column with washing solution.

In another aspect, Applicants have discovered that column separation efficiency can be preserved by storing the column separation media in the column containing a solution of multivalent cation binding agent therein. The solution of binding agent may also contain a counterion agent. Any of the multivalent cation binding agents, counterion agents, and solvents described hereinabove are suitable for the purpose of storing a MIPC column. In a preferred embodiment, a column packed with MIPC separation media is stored in an organic solvent containing a multivalent cation binding agent and a counterion agent. An example of this preferred embodiment is 0.032 M EDTA and 0.1 M TEAA in 25% aqueous acetonitrile. In preparation for storage, a solution of multivalent cation binding agent, as described above, is passed through the column for about 30 minutes. The column is then disconnected from the HPLC apparatus and the column ends are capped with commercially available threaded end caps made of material which does not release multivalent cations. Such end caps can be made of coated stainless steel, titanium, organic polymer or any combination thereof.

Figure 22:
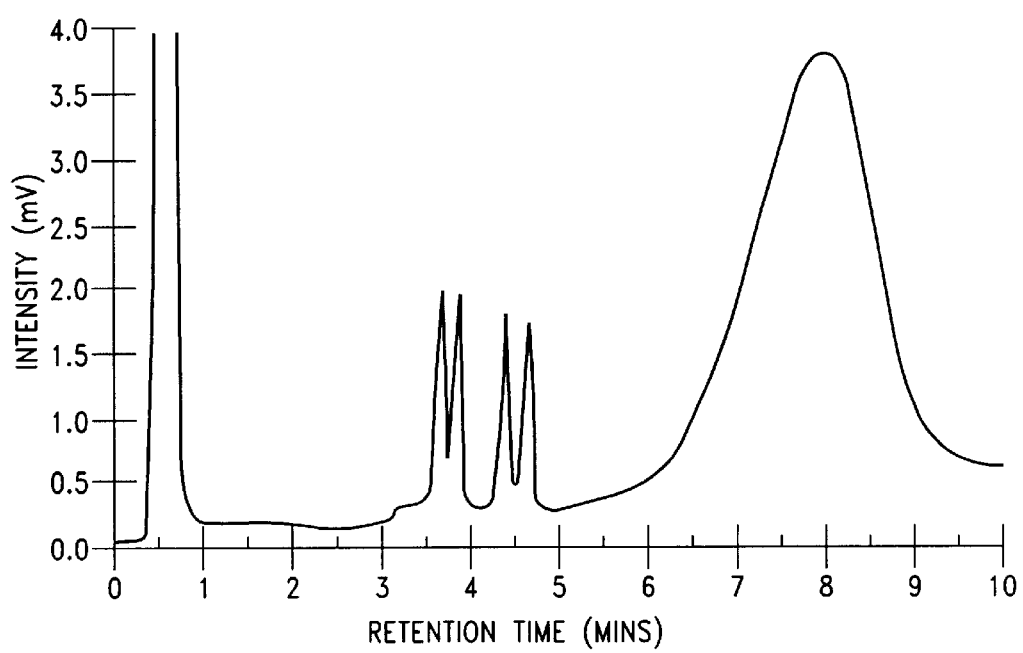
FIG. 22 is an elution profile of another injection of the same 209 bp mixture and using the same column as in FIG. 21, but after flushing the column with 0.1 M TEAA, 25% acetonitrile, and 0.32 M EDTA for 45 minutes at 75° C.
Figure 20:
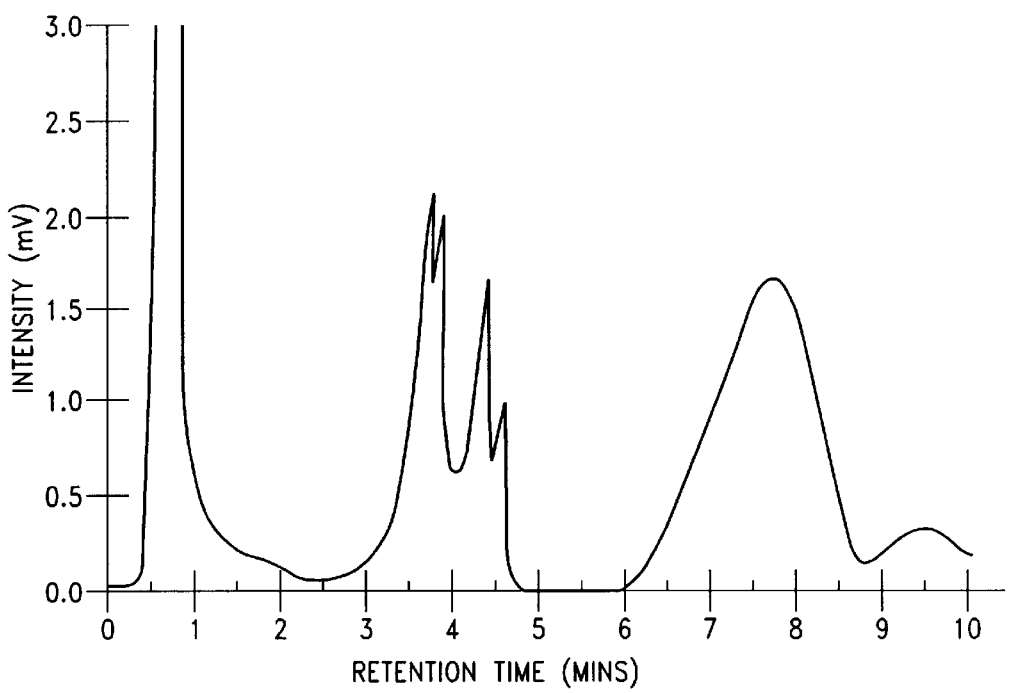
FIG. 20 is an elution profile showing separation of a 209 base pair homoduplex/heteroduplex standard mutation detection mixture performed by DMIPC at 56° C.

The effectiveness of the surprising discovery made by Applicants, that washing a MIPC column with a multivalent cation binding agent restores the ability of the column to separate heteroduplexes and homoduplexes in mutation detection protocols under DMIPC conditions, is described in Example 18 and demonstrated in FIGS. 20, 21, and 22. As described in Example 18, Applicants noticed a decrease in resolution of homoduplexes and heteroduplexes during the use of a MIPC column in mutation detection. However, no apparent degradation in resolution was observed when a DNA standard containing pUC18 HaeIII digest (Sigma/Aldrich Chemical Co.) was applied at 50° C. (not shown). In order to further test the column performance, a mixture of homoduplexes and heteroduplexes in a 209 bp DNA standard was applied to the column under DMIPC conditions of 56° C. (Kuklin et al., *Genetic Testing* 1:201 (1998). It was surprisingly observed the peaks representing the homoduplexes and heteroduplexes of the mutation detection standard were poorly resolved (FIG. 20).

FIG. 21 shows some improvement in the separation of homoduplexes and heteroduplexes of the standard mutation detection mixture when a guard cartridge containing cation capture resin was deployed in line between the solvent reservoir and the MIPC system. The chromatography shown in FIG. 21 was performed at 56° C. The column used in FIG. 21 was the same column used in the separation shown in FIG. 20 and for separating the standard pUC18 HaeIII digest.

FIG. 22 shows the separation of homoduplexes and heteroduplexes of the standard mutation detection mixture at 56° C. on the same column used to generate the chromatograms in FIGS. 20 and 21. However, in FIG. 22 the column was washed for 45 minutes with a solution comprising 32 mM EDTA and 0.1 M TEAA in 25% acetonitrile at 75° C. prior to sample application. FIG. 22 shows four cleanly resolved peaks representing the two homoduplexes and the two heteroduplexes of the standard 209 bp mutation detection mixture. This restoration of the separation ability, after washing with a solution containing a cation binding agent, of the MIPC column under DMIPC conditions compared to the chromatograms of FIGS. 20 and 21 clearly shows the effectiveness and the utility of the present invention.

In an important aspect of the present invention, Applicants have developed a standardized criteria to evaluate the performance of a DMIPC separation media. DMIPC as used herein, is defined as a process for separating heteroduplexes and homoduplexes using a non-polar separation medium (e.g., beads or rod) in the column, wherein the process uses a counterion agent, and an organic solvent to desorb the nucleic acid from the medium, and wherein the medium is characterized as having a Mutation Separation Factor (MSF) of at least 0.1. In one embodiment, the medium has a Mutation Separation Factor of at least 0.2. In a preferred embodiment, the medium has a Mutation Separation Factor of at least 0.5. In an optimal embodiment, the medium has a Mutation Separation Factor of at least 1.0.

The performance of the column is demonstrated by high efficiency separation by DMIPC of heteroduplexes and homoduplexes. Applicants have found that the best criterion for measuring performance is a Mutation Separation Factor as described in Example 17. This is measured as the difference between the areas of the resolved heteroduplex and homoduplex peaks. A correction factor may be applied to the generated areas underneath the peaks. The following aspects may affect the calculated areas of the peaks and reproducibility of the same: baseline drawn, peak normalization, inconsistent temperature control, inconsistent elution conditions, detector instability, flow rate instability, inconsistent PCR conditions, and standard and sample degradation. Some of these aspects are discussed by Snyder, et al., in Introduction to *Modern Liquid Chromatography*, $2^{nd}$ Ed., John Wiley and Sons, pp. 542–574 (1979) which is incorporated by reference herein.

The Mutation Separation Factor (MSF) is determined by the following equation:

$$MSF = (area\ peak\ 2 - area\ peak\ 1)/area\ peak\ 1$$

where area peak 1 is the area of the peak measured after DMIPC analysis of wild type and area peak 2 is the total area of the peak or peaks measured after DMIPC analysis of a hybridized mixture containing a putative mutation, with the hereinabove correction factors taken into consideration, and where the peak heights have been normalized to the wild type peak height. Separation particles are packed in an HPLC column and tested for their ability to separate a standard hybridized mixture containing a wild type 100 bp Lambda DNA fragment and the corresponding 100 bp fragment containing an A to C mutation at position 51.

High pressure pumps are used for pumping mobile phase in the systems described in U.S. Pat. No. 5,585,236 to Bonn and in U.S. Pat. No. 5,772,889 to Gjerde. It will be appreciated that other methods are known for driving mobile phase through separation media and can be used in carrying out the separations of polynucleotides as described in the present invention. A non-limiting example of such an alternative method includes "capillary electrochromatography" (CEC) in which an electric field is applied across capillary columns packed with microparticles and the resulting electroosmotic flow acts as a pump for chromatography. Electroosmosis is the flow of liquid, in contact with a solid surface, under the influence of a tangentially applied electric field. The technique combines the advantages of the high efficiency obtained with capillary electrophoretic separations, such as capillary zone electrophoresis, and the general applicability of HPLC. CEC has the capability to drive the mobile phase through columns packed with chromatographic particles, especially small particles, when using electroosmotic flow. High efficiencies can be obtained as a result of the plug-like flow profile. In the use of CEC in the present invention, solvent gradients are used and rapid separations can be obtained using high electric fields. The following references describing CEC are each incorporated in their entirety herein: Dadoo, et al, LG-GC 15:630 (1997); Jorgenson, et al., *J. Chromatog.* 218:209 (1981); Pretorius, et al., *J. Chromatog.* 99:23 (1974); and the following U.S. Pat. Nos. to Dadoo 5,378,334 (1995), 5,342,492 (1994), and 5,310,463 (1994). In the operation of this aspect of the present invention, the capillaries are packed, either electrokinetically or using a pump, with the separation beads described in the present specification. In another embodiment, a polymeric rod is prepared by bulk free radical polymerization within the confines of a capillary column. Capillaries are preferably formed from fused silica tubing or etched into a block. The packed capillary (e.g., a 150-μm i.d. with a 20-cm packed length and a window located immediately before the outlet frit) is fitted with frits at the inlet and outlet ends. An electric field, e.g., 2800V/cm, is applied. Detection can be by uv absorbance or by fluorescence. A gradient of organic solvent, e.g., acetonitrile, is applied in a mobile phase containing counterion agent (e.g. 0.1 M TEAA). to elute the polynucleotides. The column temperature is maintained by conventional temperature control means. In the preferred embodiment, all of the precautions for minimizing trace metal contaminants as described hereinabove are employed in using CEC.

In a related method, mixtures of polynucleotides are separated on thin layer chromatography (TLC) plates. In this method, the beads of the present invention are mixed with a binder and bound to a TLC plate by conventional methods (Remington: *The Science and Practice of Pharmacy*, $19^{th}$ *Edition*, Gennaro ed., Mack Publishing Co. (1995) pp. 552–554). A fluorophore is optionally included in the mixture to facilitate detection. The sample is spotted on the plate and the sample is run isocratically under capillary flow. In a preferred embodiment, the sample is run under electroosmotic flow in a process called High-Speed TLC (HSTLC). In the case of HSTLC, the plate is first wetted with solvent (e.g., acetonitrile solution in the presence of counterion agent) and an electric field (e.g., 2000 V/cm) is applied. Solvent accumulating at the top of the plate is removed by suction.

Applicants have surprisingly discovered that dsDNA of selected ranges of base pair length are separable under isocratic conditions by MIPC using the beads of the present invention as described in Example 6. The isocratic mobile phase conditions for separating a selected range of DNA base pair length, as determined using MIPC, are used in the TLC and HSTLC methods.

Other features of the invention will become apparent in the course of the following descriptions of exemplary embodiments which are given for illustration of the invention and are not intended to be limiting thereof.

All references cited herein are hereby incorporated by reference in their entirety.

Procedures described in the past tense in the examples below have been carried out in the laboratory. Procedures described in the present tense have not been carried out in the laboratory, and are constructively reduced to practice with the filing of this application.

EXAMPLE 1

C-18 Bonded Phase Standard Phase

To a 1000-mL round bottomed flask, add 200 g of nonporous, 2 μm silica and one small stirring egg. Transfer flask with silica to an oven and heat at 125° C. overnight (i.e., at least 8 hours). Have heating mantle and condenser set up.

The C-18 bonding reagent, n-octadecyldimethylsilane, is a waxy white solid to semi-solid at room temperature. To transfer, open the bottle in a hood and gently warm with a heat gun (note: pressure can build up in stored chlorosilane bottles, and they should be handled as if they were HCI, as upon contact with moisture, HCI is the side product).

To a second flask, transfer 125 g of the n-octadecylmethylchlorosilane reagent, 10 mL of chloroform, 400 mL of toluene, and 65 mL of pyridine. Mix the liquid reagents by swirling, and then add to the dried silica and swirl until all of the silica is suspended. Attach the reflux condenser and bring the mixture to reflux for 15 hours. Let the mixture cool, such that refluxing has stopped. Add the capping reagent package of 20 mL of trimethylchlorosilane, 6 mL of hexamethylsilane in 20 mL of toluene. Resuspend the mixture and bring the system back to reflux for 6 hours. Let the mixture cool to room temperature.

Transfer to a Buchner funnel and wash with three 200-mL aliquots of methanol, followed by three 200-mL aliquots of acetone. Air dry for at least 0.5 hour, and then dry in the oven at 100° C. overnight.

Submit sample for elemental analysis, and percent carbon.

Dried bonded phase is now ready for column packing.

EXAMPLE 2

CN Bonded Phase, Cyano Phase

To a 1000-mL round-bottomed flask, add 200 g of nonporous, 2 μm silica, one stirring egg, and place in an oven at 125° C. overnight (i.e., at least 8 hours) to dry. To the dried silica, add 100 mL of the 3-cyanopropylmethyldichlorosilane, 10 mL of chloroform, 450 mL of toluene, and 50 mL of pyridine. Suspend the mixture and bring to reflux for 15 hours. Cool filter and wash in a Buchner funnel with one 200-mL aliquot of toluene, followed by two 200-mL aliquots of methanol. Transfer to a beaker and add 300 mL of 50:50 methanol:water, pH 5.5 with HCl. Suspend and let sit at room temperature for 1 hour. Filter onto Buchner funnel and wash phase with methanol and acetone. Transfer to the 1000-mL round-bottomed flask and dry in oven overnight.

Next, endcap by adding 20 mL of trimethylchlorosilane, 6 mL of hexamethyl-disilane, 350 mL of toluene, 10 mL of chloroform, and 25 mL of pyridine to the dried bonded phase, and bring to reflux for 6 hours. Cool the resulting mixture, transfer to a Buchner funnel, and wash with three 200-mL aliquots of methanol, followed by three 200-mL aliquots of acetone. Air dry for at least 0.5 hour, and then dry in the oven at 100° C. overnight.

Submit a sample for elemental analysis.

The bonded phase is now ready for column packing.

EXAMPLE 3

Dioctyl Silyl Phase - C-8X2

Repeat all of the steps for CN bonded phase, but replace 3-cyanopropylmethyldichlorosilane with 100 mL of dioctyidichlorosilane.

EXAMPLE 4

Acid Wash Treatment

The procedures of Example 1 are repeated but the silica is washed with 500 mL of 100 mM HCl and then water prior to drying. The product is washed with 500 mL of 1009 mM HCl after cooling and prior to the methanol wash.

EXAMPLE 5

The product of Example 1 is coated with 100 mL of dichloromethane containing 1 gram of divinylbenzene and 10 mg of benzoylperoxide. The dichloromethane is removed by rotary evaporation until the monomer is coated onto the beads. While rotating very slowly, the temperature is increased to 70° C. for 8 hours. The product is washed with methanol.

This procedure is repeated with the product of Example 4.

EXAMPLE 6

The procedure of Example 5 is repeated with stearyidivinyl benzene in place of divinylbenzene. This procedure is repeated with the product of Example 4.

EXAMPLE 7

Fifteen (15) grams of the nonporous silica particles, 50 mL of 2,2,4-trimethylpentane, and 25 mL of vinyltrichlorosilane are refluxed for 2 hours. The modified silica is then washed several times with both 2,2,4-trimethylpentane and acetone and dried at 80° C.

Five (5) grams of the vinyl-coated silica particles prepared as described above are placed in a round bottom flask. Twenty-five mL of acetonitrile containing 2 g of a vinyl monomer (divinylbenzene, styrene, acrylonitrile, acrylic acid, butyl methacrylate, or 2-hydroxy methacrylate) are added and the mixture well dispersed. Twenty-five mL of acetonitrile containing 0.2 g of dibenzoyl peroxide is added, and the mixture is refluxed for 2 hours.

The products are extracted with acetonitrile and then acetone to remove unreacted monomers and oligomers from the particle.

In the case of the acrylic acid-modified silica, extractions with water are also carried out.

The packing materials are dried at 80° C. prior to packing.

EXAMPLE 8

Standard Procedure for Testing the Performance of Sepatation Media

Separation particles are packed in an HPLC column and tested for their ability to separate a standard DNA mixture. The standard mixture is a pUC18 DNA-HaeIII digest (Sigma-Aldrich, D6293) which contains 11 fragments having 11, 18, 80, 102, 174, 257, 267, 298, 434, 458, and 587 base pairs, respectively. The standard is diluted with water and five μL, containing a total mass of DNA of 0.25 μg, is injected.

Depending on the packing volume and packing polarity, the procedure requires selection of the driving solvent concentration, pH, and temperature. The separation conditions are adjusted so that the retention time of the 257, 267 peaks is about 6 to 10 minutes. Any one of the following solvents can be used: methanol, ethanol, 2-propanol, 1-propanol, tetrahydrofuran (THF), or acetonitrile. A counter ion agent is selected from trialkylamine acetate, trialkylamine carbonate, trialkylamine phosphate, or any other type of cation that can form a matched ion with the polynucleotide anion.

As an example of this procedure, FIG. 4 shows the high resolution of the standard DNA mixture using octadecyl modified, nonporous poly(ethylvinylbenzene-divinylbenzene) beads. The separation was conducted under the following conditions: Eluent A: 0.1 M TEAA, pH 7.0; Eluent B: 0.1 M TEAA, 25% acetonitrile; Gradient:

| Time (min) | % A | % B |
|---|---|---|
| 0.0 | 65 | 35 |
| 3.0 | 45 | 55 |
| 10.0 | 35 | 65 |
| 13.0 | 35 | 65 |
| 14.0 | 0 | 100 |
| 15.5 | 0 | 100 |
| 16.5 | 65 | 35 |

The flow rate was 0.75 mL/min, detection UV at 260 nm, column temp. 50° C. The pH was 7.0.

Figure 5:
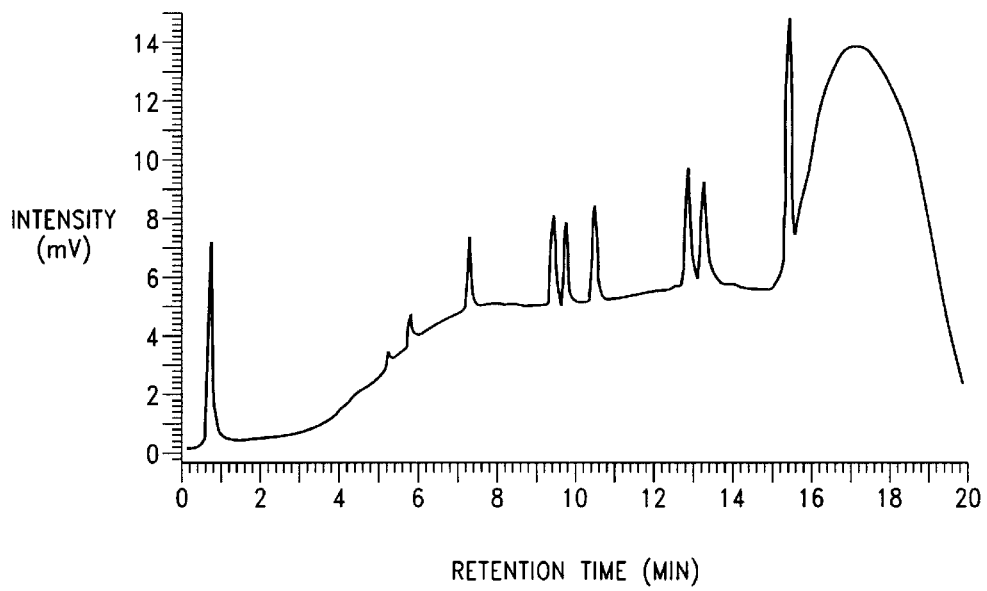
FIG. 5 is a MIPC separation of pUC18 DNA-HaeII digestion fragments on a column containing nonporous 2.1 micron beads of underivatized poly(styrene-divinylbenzene).

As another example of this procedure using the same separation conditions as in FIG. 4, FIG. 5 is a high resolution separation of the standard DNA mixture on a column containing nonporous 2.1 micron beads of underivatized poly(styrene-divinylbenzene).

EXAMPLE 9

This example demonstrates the high resolution separation of DNA restriction fragments using octadecyl modified, nonporous silica reverse phase material, as described in Example 1. The experiment is conducted under the following conditions: Column: 50×4.6 mm i.d. Mobile phase: 0.1 M TEAA, pH 7.0. Gradient: 8.75–11.25% acetonitrile in 2 minutes, followed by 11.25–14.25% acetonitrile in 10 minutes, 14.5–15.25% acetonitrile in 4 minutes, and by 15.25–16.25% acetonitrile in 4 minutes. Flow rate 1 mL/min. Column temperature: 50° C. Detection: UV at 254 nm. Sample: Mixture of 0.75 µg pBR322 DNA-HaeIII restriction digest and 0.65 µg Φ174 DNA-Hinc II restriction digest.

A high resolution separation is obtained by optimizing the concentration of triethylammonium acetate (TEAA), shape of the gradient curve, column temperature, and flow rate. The resolution of peaks is continuously enhanced in going from 25 mM to at least 125 mM of TEAA. The gradient is optimized by decreasing the steepness of the gradient curve with increasing fragment lengths of DNA molecules. The best separations of double-stranded DNA molecules are accomplished at about 30° C. to 50° C. Denaturation of DNA at higher than about 50° C. prevents utilization of higher column temperatures for double-stranded DNA fragments, although single-stranded DNA separations can be performed at temperatures up to 80° C. and higher.

EXAMPLE 10

If the gradient delay volume is minimized, the separation of PCR products and hybrid DNA derived from various sources of DNA, including living and dead organisms (animal and plant), as well as parts of such organisms (e.g., blood cells, biopsies, sperm, etc.) on octadecyl modified, nonporous poly-(ethylvinylbenzene-divinylbenzene) coated beads can be achieved with run times under 2 minutes.

The analysis of PCR products and hybrid DNA usually requires only separation and detection of one or two species of known length. Because of this, the resolution requirements are considerably less severe than for separations of DNA restriction fragments. Such less stringent resolution requirements allow the utilization of steep gradients and, consequently, lead to still shorter run times. The recovery rate for a DNA fragment containing 404 base pairs is about 97.5%.

Unlike capillary electrophoresis (CE), PCR samples do not have to be desalted prior to analysis by MIPC. This represents a decisive advantage of MIPC over GE. With MIPC, it is thus possible to achieve a fully automated analysis of PCR samples if an automatic autosampler is utilized. Moreover, since the volume of sample injection is known, in contrast to CE, quantitation over several orders of magnitude can be achieved without the need for an internal standard, hence allowing the quantitation of gene expression, as well as the determination of virus titers in tissues and body fluids. A fully automated version of the method of the invention can be used to discriminate (distinguish) normal from mutated genes, as well as to detect oncogenes, bacterial and viral genome polynucleotides (hepatitis C virus, HIV, tuberculosis) for diagnostic purposes. Moreover, adjustment of column temperature allows one to moderate the stringency of hybridization reactions or to separate heteroduplex from homoduplex DNA species.

The suitability of the polymer-coated beads of the invention for clinical use is described under the following conditions: Column: 50×4.6 mm i.d. Mobile phase: 0.1 M TEAA, pH 7.0. Gradient: 11.25–13.75% acetonitrile in 1 minute, followed by 22.5% acetonitrile for 6 seconds, and 11.25% acetonitrile for 54 seconds. Flow rate: 3 mL/min. Column temperature: 50° C. Detection: UV at 256 nm. Sample: 20 µl of a PCR sample. In the separation, the following elution order is obtained: 1=unspecific PCR product, 2=PCR product having 120 base pairs, 3=PCR product having 132 base pairs, and 4=PCR product having 167 base pairs.

PCR methods and processes are described by R. K. Saiki et al. in Science, 23):1350-1354 (1985) and K. B. Mullis in U.S. Patent No. 4,863,202. These references are incorporated herein by reference for a more complete description of methods and processes for obtaining PCR samples which can be separated using the method of the present invention.

The repetitive analysis of PCR products using the method of the invention is highly reproducible under the described analytical conditions. The results are not in any way influenced by the preceding injection. The present method is highly suitable for routine use under real conditions in clinical laboratories.

EXAMPLE 11

The following describes a separation of single-stranded DNA. A silica-column, as described in Example 1, 1.5 micron, 30×4.6 mm i.d., is used with a linear gradient of 2.5 - 12.5% acetonitrile in 0.1 M triethylammonium acetate in 40 minutes at 1 mL/min and 40° C. A mixture of p(dC)12-18 and p(dT)12-18 oligonucleotides is separated, with the first mixture eluting between 5 and 15 minutes, and the second mixture eluting between 15 and 30 minutes.

EXAMPLE 12

Sorption Enthalpy Measurements

Figure 6:
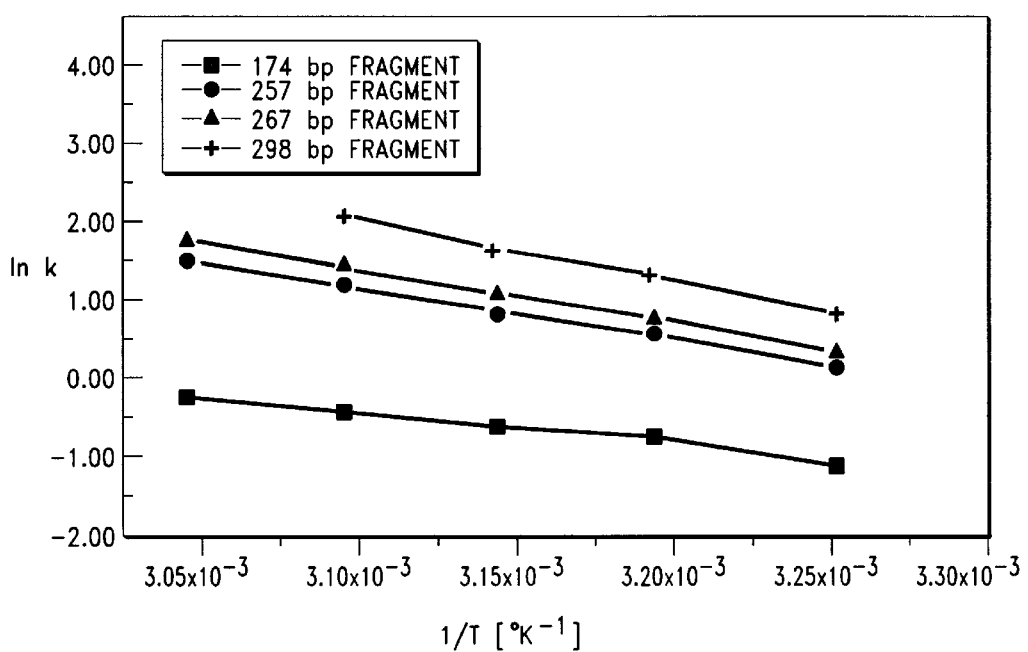
FIG. 6 is a Van't Hoff plot of the retention factor $1/T[°K^{-1}]$ with alkylated poly(styrene-divinylbenzene) beads showing positive enthalpy using acetonitrile as the solvent.

Four fragments (174 base pair, 257 base pair, 267 base pair, and 298 base pair, found in 5 µl pUC18 DNA-HaeIII digest, 0.04 µg DNA/µl) of a DNA digest are separated under isocratical conditions at different temperatures using C-1 8 alkylated poly(styrene-divinylbenzene) polymer beads. Conditions used for the separation are: Eluent: 0.1 M triethylammonium acetate, 14.25% (v/v) acetonitrile at 0.75 mL/min, detection at 250 nm UV, temperatures at 35, 40, 45, 50, 55, and 60° C., respectively. A plot of In k versus 1/T (FIG. 6) shows that the retention factor k is increasing with increasing temperature. This indicates that the retention mechanism is based on an endothermic process ($\Delta H_{sorp} > 0$).

Figure 7:
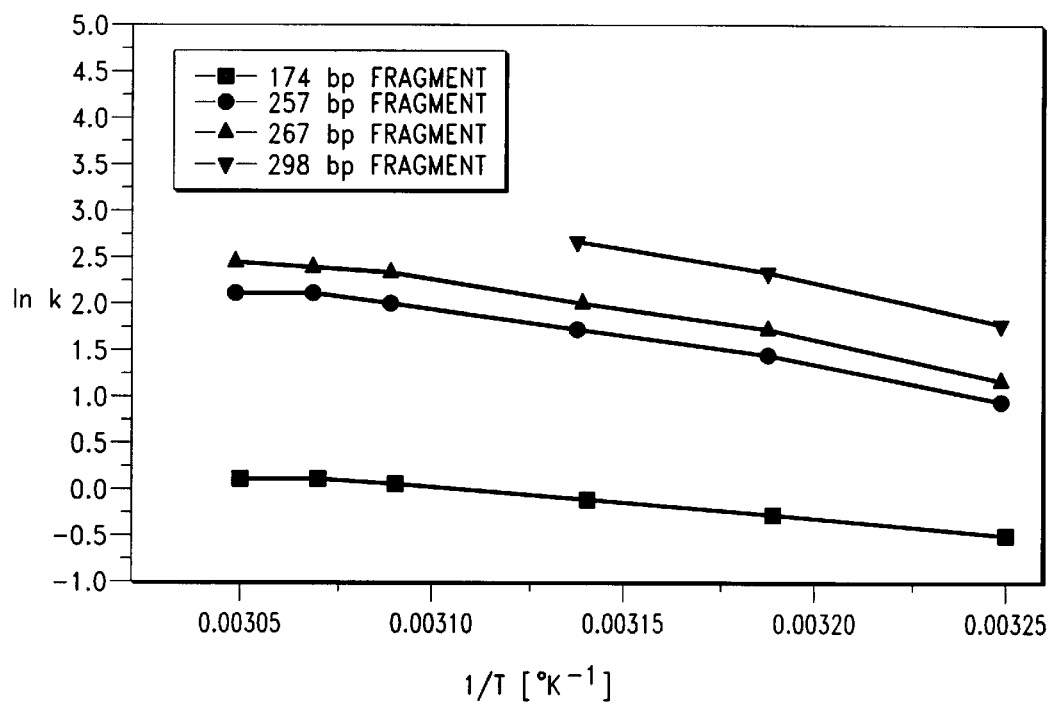
FIG. 7 is a Van't Hoff plot of the retention factor $1/T[°K^{-1}]$ with underivatized poly(styrene-divinylbenzene) beads showing positive enthalpy using acetonitrile as the solvent.

The same experiments on non-alkylated poly(styrene-divinylbenzene) beads (FIG. 7) give a negative slope for a plot of In k versus 1/T, although the plot is slightly curved.

Figure 8:
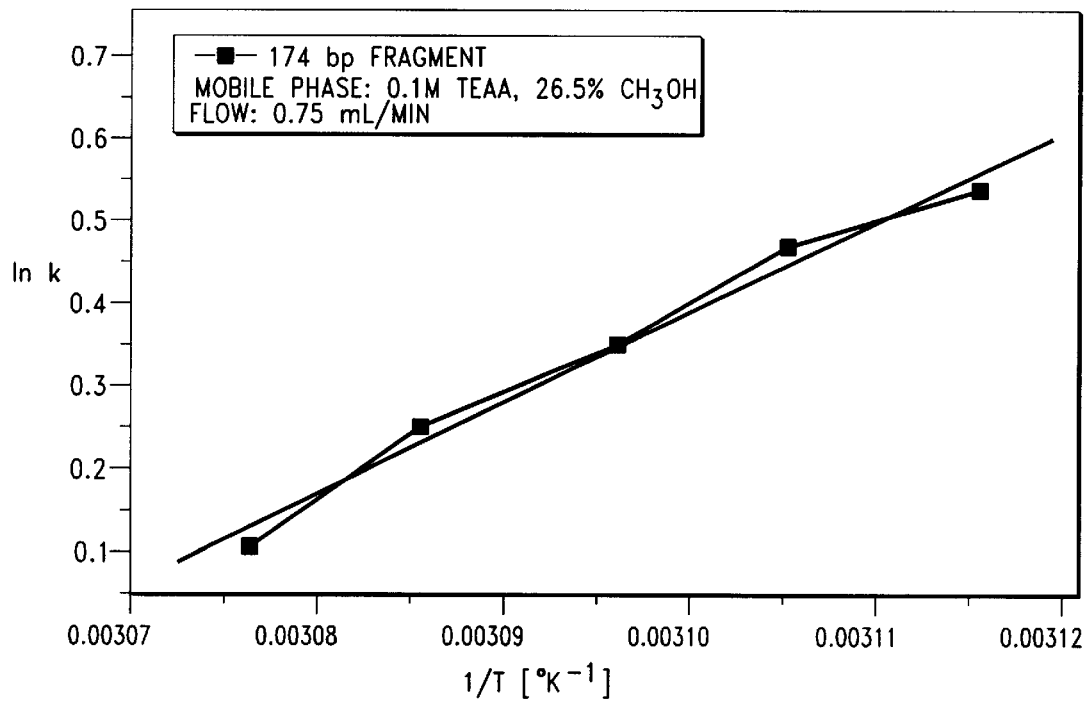
FIG. 8 is a Van't Hoff plot of the retention factor $1/T[°K^{-1}]$ with alkylated poly(styrene-divinylbenzene) beads showing negative enthalpy using methanol as the solvent.

The same experiments on alkylated poly(styrene-divinylbenzene) beads but the acetonitrile solvent is substituted with methanol (FIG. 8) gives a plot In k versus 1/T shows the retention factor k is decreasing with increasing temperature. This indicates the retention mechanism is based on an exothermic process ($\Delta H_{sorp} < 0$). Replacing the alkylated and non-alkylated polymer beads with silica beads having a coating of alkylated poly(styrene-divinylbenzene) and non-alkylated alkylated poly(styrene-divinylbenzene) will give the same results.

EXAMPLE 13

Separations with alkylated poly(styrene-divinylbenzene) beads Mobile phase components are chosen to match the desorption ability of the elution solvent in the mobile phase to the attraction properties of the bead to the DNA-counter ion complex. As the polarity of the bead decreases, a stronger (more organic) or higher concentration of solvent will be required. Weaker organic solvents such as methanol are generally required at higher concentrations than stronger organic solvents such as acetonitrile.

Figure 9:
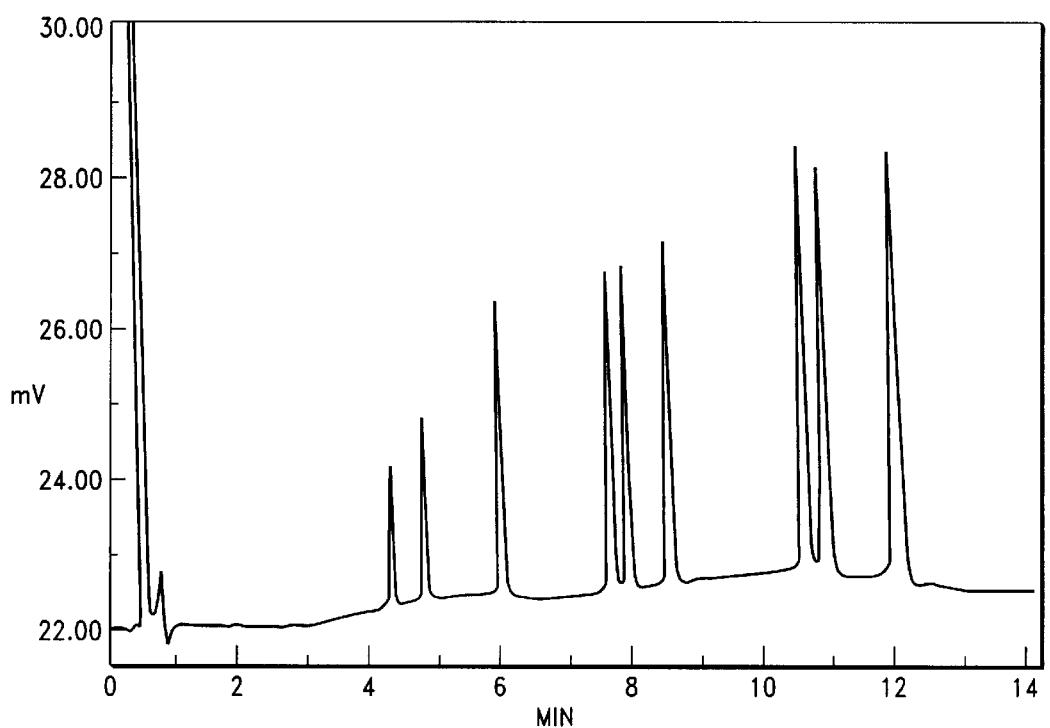
FIG. 9 is a separation using alkylated beads and acetonitrile as solvent.

FIG. 9 shows the high resolution separation of DNA restriction fragments using octadecyi modified, nonporous poly(ethylvinylbenzene-divinylbenzene) beads. The experiment was conducted under the following conditions. Column: 50×4.6 mm i.d.; mobile phase 0.1 M triethylammonium acetate (TEAA), pH 7.2; gradient: 33-55% acetonitrile in 3 min, 55-66% acetonitrile in 7 min, 65% acetonitrile for 2.5 min; 65-100% acetonitrile in 1 min; and 100-35% acetonitrile in 1.5 min. The flow rate was 0.75 ml/min, detection UV at 260 nm, column temp. 51° C. The sample was 5 μl (=0.2 μg pUC18 Hea III digest).

Figure 10:
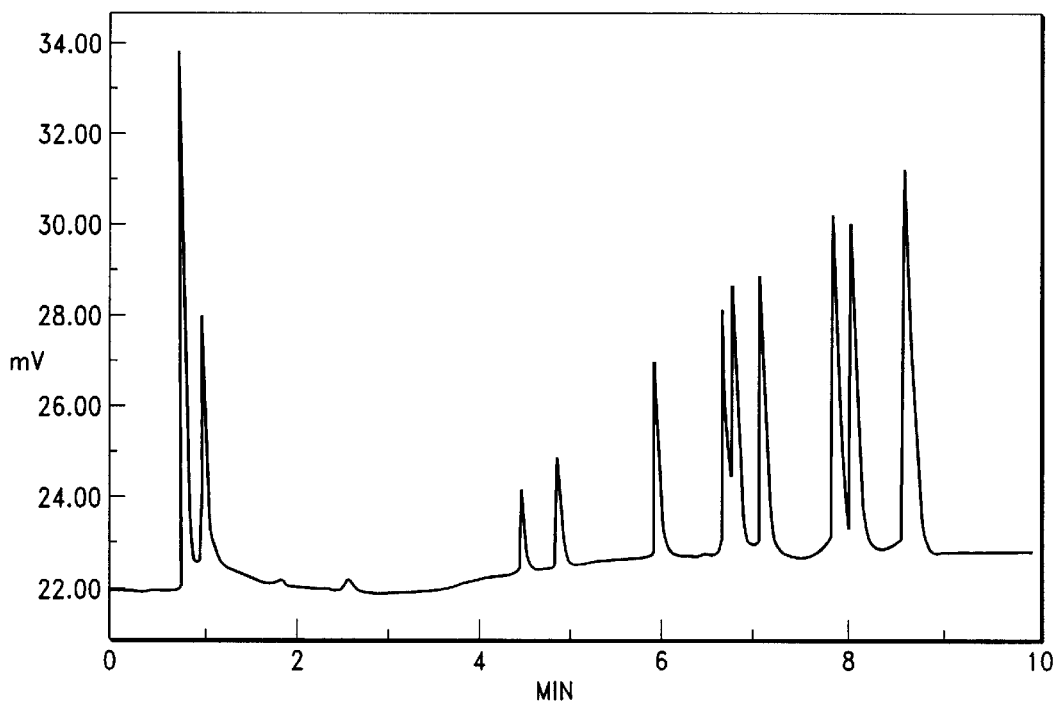
FIG. 10 is a separation using alkylated beads and 50.0% methanol as the solvent.

Repeating the above procedure replacing the acetonitrile with 50.0% methanol in 0.1 M TEAA gives the separation shown in FIG. 10.

Figure 11:
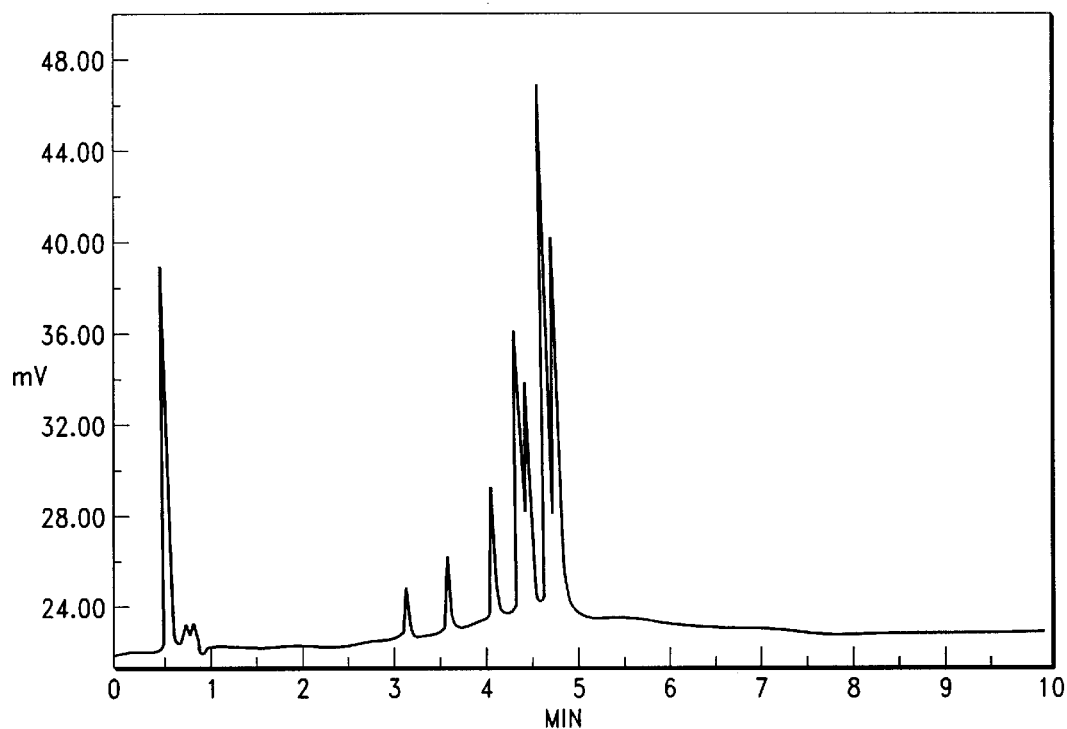
FIG. 11 is a separation using alkylated beads and 25.0% ethanol as the solvent.

Repeating the above procedure replacing the acetonitrile with 25.0% ethanol in 0.1 M TEAA gives the separation shown in FIG. 11.

Figure 12:
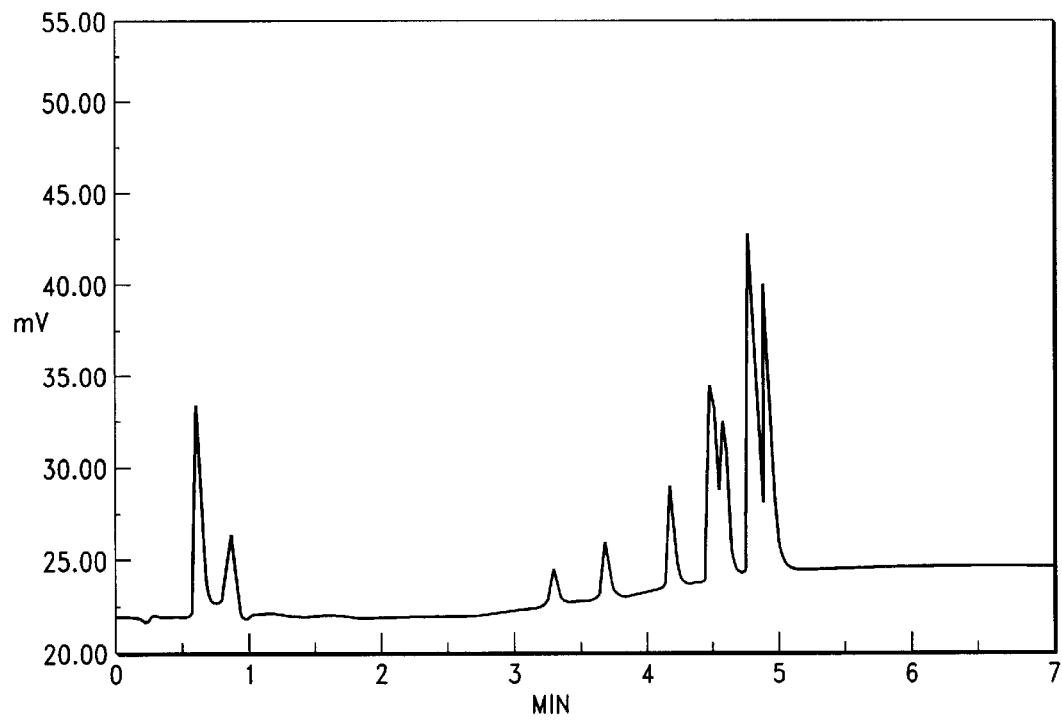
FIG. 12 is a separation using alkylated beads and 25.0% vodka (Stolichnaya, 100 proof) as the solvent.

Repeating the above procedure replacing the acetonitrile with 25% vodka (Stolichnaya, 100 proof) in 0.1 M TEAA gives the separation shown in FIG. 12.

Figure 13:
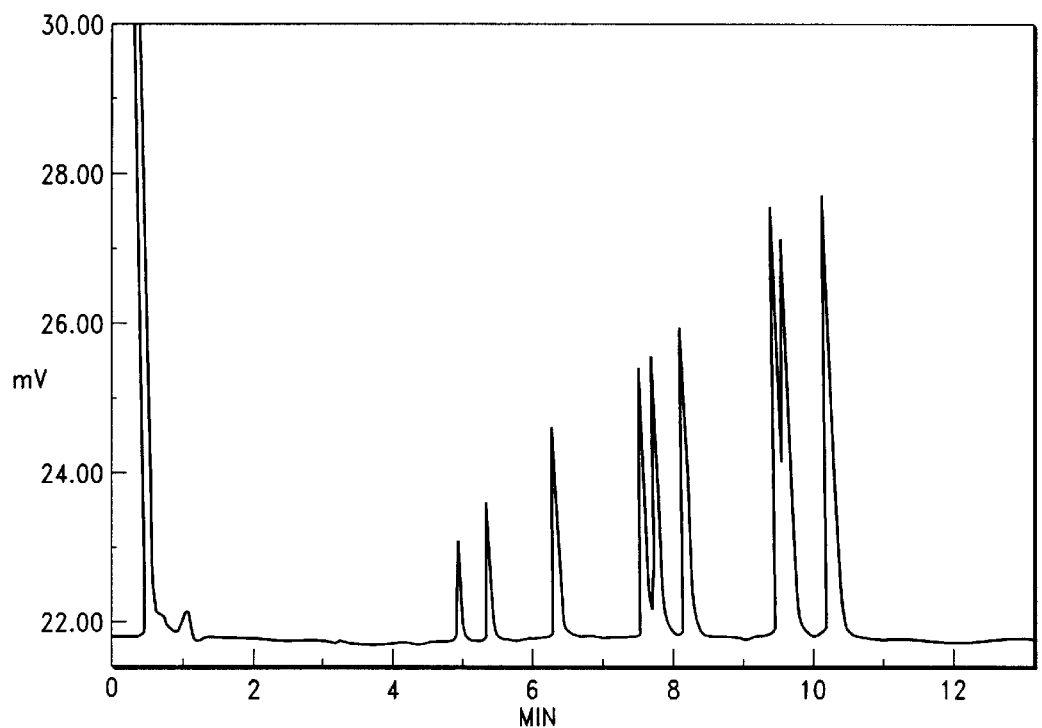
FIG. 13 is a separation using alkylated beads and 25.0% 1-propanol as the solvent.

The separation shown in FIG. 13 was obtained using octadecyl modified, nonporous poly(ethylvinylbenzene-divinylbenzene) beads as follows: Column: 50×4.6 mm i.d.; mobile phase 0.1 M TEAA, pH 7.3; gradient: 12-18% 0.1 M TEAA and 25.0% 1-propanol (Eluent B) in 3 min, 18-22% B in 7 min, 22% B for 2.5 min; 22-100% B in 1 min; and 100-12% B in 1.5 min. The flow rate was 0.75 mL/min, detection UV at 260 nm, and column temp. 51° C. The sample was 5 μl (=0.2 9 g pUC18 DNA-HaeIII digest).

Figure 14:
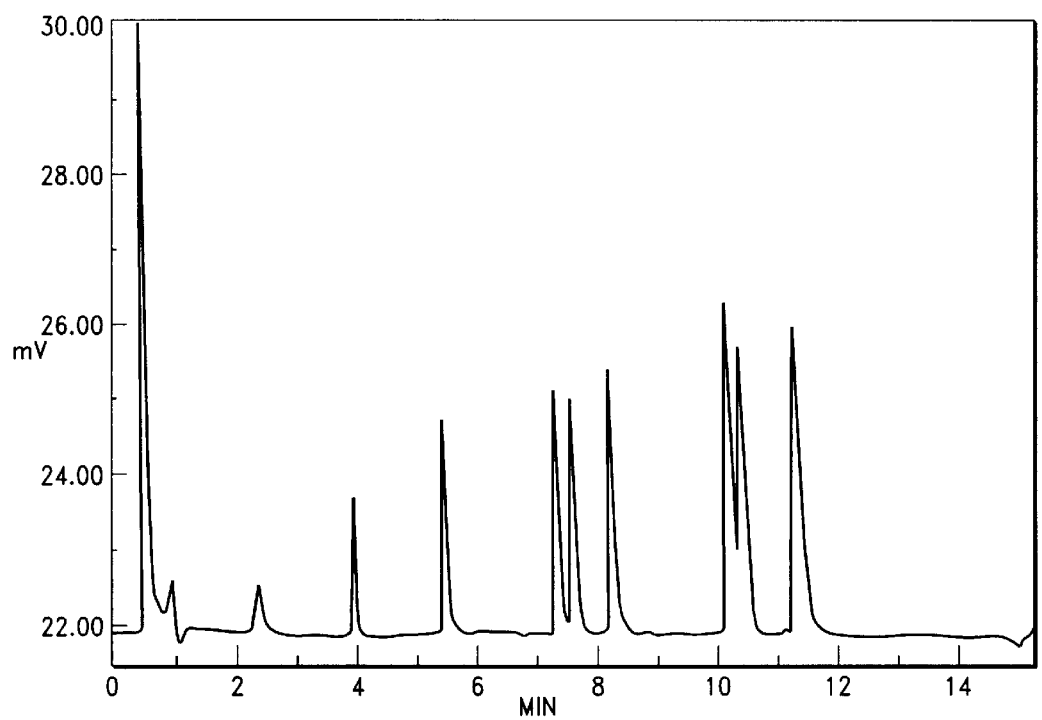
FIG. 14 is a separation using alkylated beads and 25.0% 1-propanol as the solvent.

The separation shown in FIG. 14 was obtained using octadecyl modified, nonporous poly(ethylvinylbenzene-divinylbenzene) beads as follows: Column: 50×4.6 mm i.d.; mobile phase 0.1 M TEAA, pH 7.3; gradient: 15-18% 0.1 M TEAA and 25.0% 1-propanol (Eluent B) in 2 min, 18-21% B in 8 min, 21% B for 2.5 min; 21-100% B in 1 min; and 100-15% B in 1.5 min. The flow rate was 0.75 mumin, detection UV at 260 nm, and column temp. 51° C. The sample was 5 II (=0.2 μg pUC18 DNA-HaeIII digest).

Figure 15:
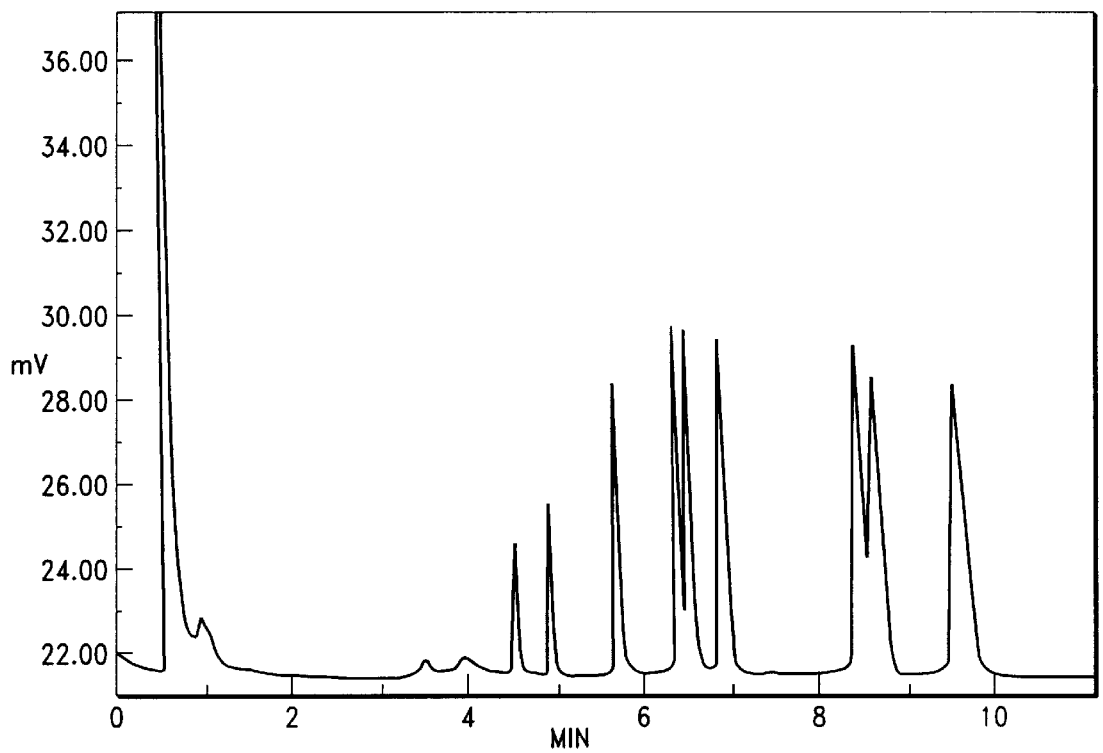
FIG. 15 is a separation using alkylated beads and 10.0% 2-propanol as the solvent.

The separation shown in FIG. 15 was obtained using octadecyl modified, nonporous poly(ethylvinylbenzene-divinylbenzene) beads as follows: Column: 50×4.6 mm i.d.; mobile phase 0.1 M TEAA, pH 7.3; gradient: 35-55% 0.1 M TEAA and 10.0% 2-propanol (Eluent B) in 3 min, 55-65% B in 10 min, 65% B for 2.5 min; 65-100% B in 1 min; and 100-35% B in 1.5 min. The flow rate was 0.75 mumin, detection UV at 260 nm, and column temp. 51° C. The sample was 5 μl (=0.2 μg pUC18 DNA-HaeIII digest).

Figure 16:
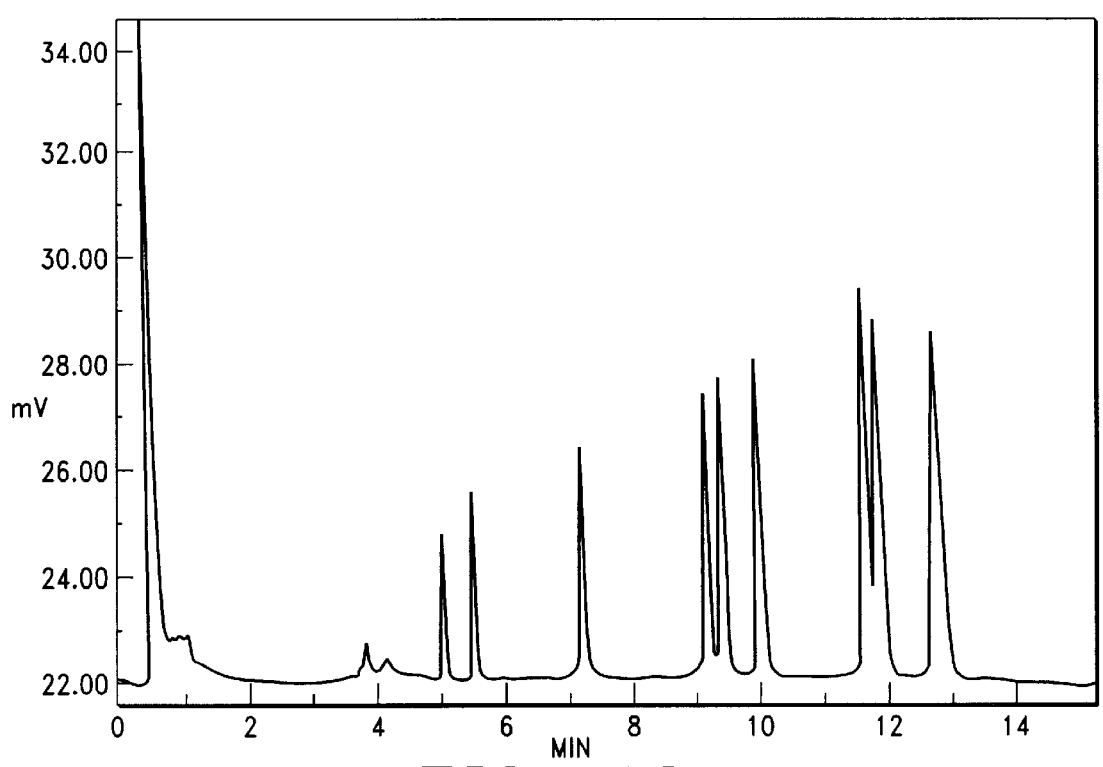
FIG. 16 is a separation using alkylated beads and 10.0% 2-propanol as the solvent.

The separation shown in FIG. 16 was obtained using octadecyl modified, nonporous poly(ethylvinylbenzene-divinylbenzene) beads as follows: Column: 50×4.6 mm i.d.; mobile phase 0.05 M TEA$_2$HPO$_4$, pH 7.3; gradient: 35-55% 0.05 M TEA$_2$HPO$_4$ and 10.0% 2-propanol (Eluent B) in 3 min, 55-65% B in 7 min, 65% B for 2.5 min; 65-100% B in 1 min; and 100-65% B in 1.5 min. The flow rate was 0.75 mL/min, detection UV at 260 nm, and column temp. 51° C. The sample was 5 1 (=0.2 μg pUC18 DNA-HaeIII digest).

Figure 17:
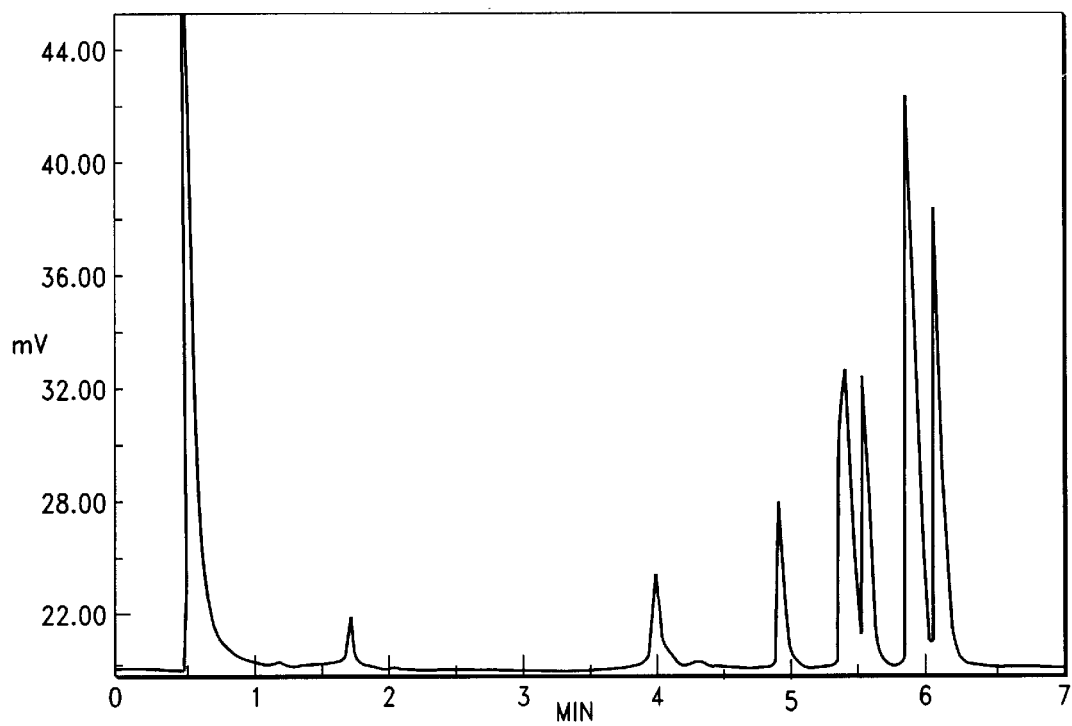
FIG. 17 is a separation using alkylated beads and 25.0% THF as the solvent.

The separation shown in FIG. 17 was obtained using octadecyl modified, nonporous poly(ethylvinylbenzene-divinylbenzene) beads as follows: Column: 50×4.6 mm i.d.; mobile phase 0.1 M TEAA, pH 7.3; gradient: 6-9% 0.1 M TEAA and 25.0% THF (Eluent B) in 3 min, 9-11% B in 7 min, 11% B for 2.5 min; 11-100% B in 1 min; and 100-6% B in 1.5 min. The flow rate was 0.75 mL/min, detection UV at 260 nm, and column temp. 51° C. The sample was 5 μl (=0.2 μg pUC18 DNA-HaeIII digest).

EXAMPLE 14

Isocratic/gradient separation of dsDNA

Figure 18:
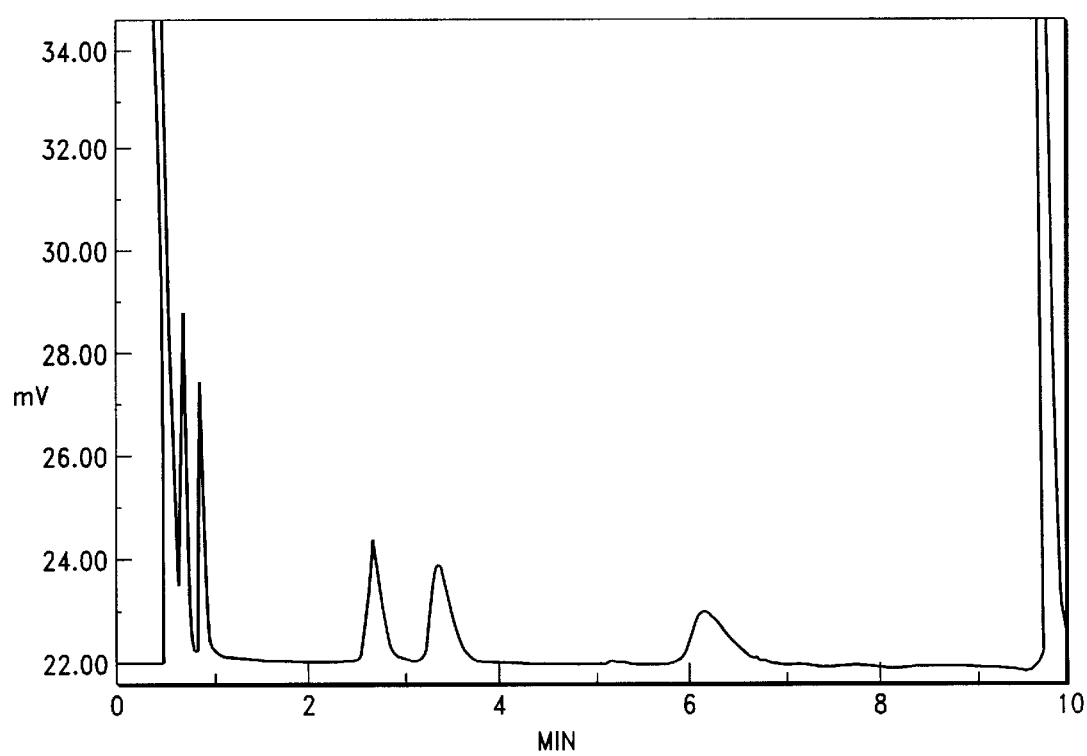
FIG. 18 is an isocratic/gradient separation on non-alkylated poly(styrene-divinylbenzene) beads.

The following is an isocratic/gradient separation of dsDNA on a polystyrene coated silica base material. Isocratic separations have not been performed in DNA separations because of the large differences in the selectivity of DNA/alkylammonium ion pair for beads. However, by using a combination of gradient and isocratic elution conditions, the resolving power of a system can be enhanced for a particular size range of DNA. For example, the range of 250-300 base pairs can be targeted by using a mobile phase of 0.1 M TEAA, and 14.25% acetonitrile at 0.75 mL/min at 40° C. on a 50×4.6 mm crosslinked polystyrene coated silica reverse phase column, 2.0 micron. The pUC18 DNA-HaeIII digest was injected under isocratic conditions and 257, 267 and 298 base pairs DNA eluted completely resolved. Then larger fragments were removed from the column with 0.1 M TEAA/25% acetonitrile at 9 minutes. FIG. 18 shows a separation using the same elution conditions but performed on a poly(styrene-divinylbenzene) polymer based column. In other examples, there might be an initial isocratic step (to condition the column), then a gradient step (to remove or target the first group of DNA at a particular size), then an isocratic step (to separate the target material of a different size range) and finally a gradient step to clean the column.

EXAMPLE 15

Preparation of a silica monolith

All the gel samples are prepared by hydrolyzing tetramethoxysilane (TMOS) with 0.01 M aqueous solution of acetic acid in the presence of poly(ethylene oxide)(PEO), with an average molecular weight of 10,000. The PEO containing system is chosen because it gives relatively high macropore volume and exhibits less sensitive dependence of pore size on compositional parameters. The constituents are mixed together in an ice cooled container and stirred vigorously for 5 min, while the hydrolysis gradually proceeds and the heterophase mixture is homogenized due to the liberation of alcohol. The solution is then degassed under ultrasonic radiation, and is poured into plastic cylinders with inner diameter of 10 mm. The solution is then kept at constant temperatures for gelation and aging, in a tightly closed container. The well-aged gels are subsequently immersed in a 0.2M aqueous ammonia solution for 10 days to exchange the solvent phase, then dried at 60° C. for 3 days and finally heat treated at 600° C. for 2 h. The chemical modification with octadecyl (hereafter denoted as C18) and methyl ligands of the inner surface of the gel samples thus prepared is carried out according to the method reported below.

The base silica has a nominal through pore diameter of 5 μm and a substrate pore size of 110 angstroms. The following synthesis procedure is employed: the silica gel is first dried at 150° C. for 2 hours, then dried under reduced pressure (30 mm Hg) for an additional 2 hours. The derivatization reactions are performed with 10 g of silica gel and 8.5 micromol/m$^2$ equivalents of silane compound in pyridine and toluene. Trichlorooctadecylsilane is used for the preparation of trifunctional phases, dichloromethyloctadecylsilane for difunctional phases, and moncholorodimethyloctadecylane for monofunctional phases. The mixture of silica gel and silane are refluxed for 5 hours at 100° C. in toluene. After cooling, the packings are dispersed in chloroform, filtered, and washed several lines with chloroform. The final packings are dried at 80° C. for 8 hours. Erndcapping is performed using 8.5 micromol/m$^2$ equivalents of trimethylchlorosilane and hexamethyidisilazane under refluxing pyridine and toluene for 5 hours. The liquid chromatographic measurements are carried out for the gel rods coherently clad with thermoshrinking PTFE resin and equipped with suitable connection devices.

EXAMPLE 16

Acid Wash Treatment TQ Remove Multivalent Metal Cation Contaminants

The non-polar, derivatized silica monolith column is washed by flowing tetrahydrofuran through the column at a flow rate of 2 mL per minute for 10 minutes followed by flowing methanol through the column at 2 mL per minute for 10 minutes. The non-polar monolith column is washed further by flowing a mixture containing 100 mL of tetrahydrofuran and 100 mL of concentrated hydrochloric acid through the column at 10 mL per minute for 20 minutes. Following this acid treatment, the monolith column is washed by flowing tetrahydrofuran/water (1:1) through the column at 2 mL per minute until neutral (pH 7).

EXAMPLE 17

Determination of the Mutation Separation Factor

The Mutation Separation Factor (MSF) is determined by the following equation:

$$MSF = (area\ peak\ 2 - area\ peak\ 1)/area\ peak\ 1$$

where area peak 1 is the area of the peak measured after DMIPC analysis of wild type and area peak 2 is the total area of the peak or peaks measured after DMIPC analysis of a hybridized mixture containing a putative mutation, with the hereinabove correction factors taken into consideration, and where the wild type peak heights have been normalized to the wild type peak height. Separation particles are packed in an HPLC column and tested for their ability to separate a standard hybridized mixture containing a wild type 100 bp Lambda DNA fragment and the corresponding 100 bp fragment containing an A to C mutation at position 51.

Depending on the packing volume and packing polarity, the procedure requires selection of the driving solvent concentration, pH, and temperature. Any one of the following solvents can be used: acetonitrile, tetrahydrofuran, methanol, ethanol, or propanol. Any one of the following counterion agents can be used: trialkylamine acetate, trialkylamine carbonate, and trialkylamine phosphate.

Figure 24:
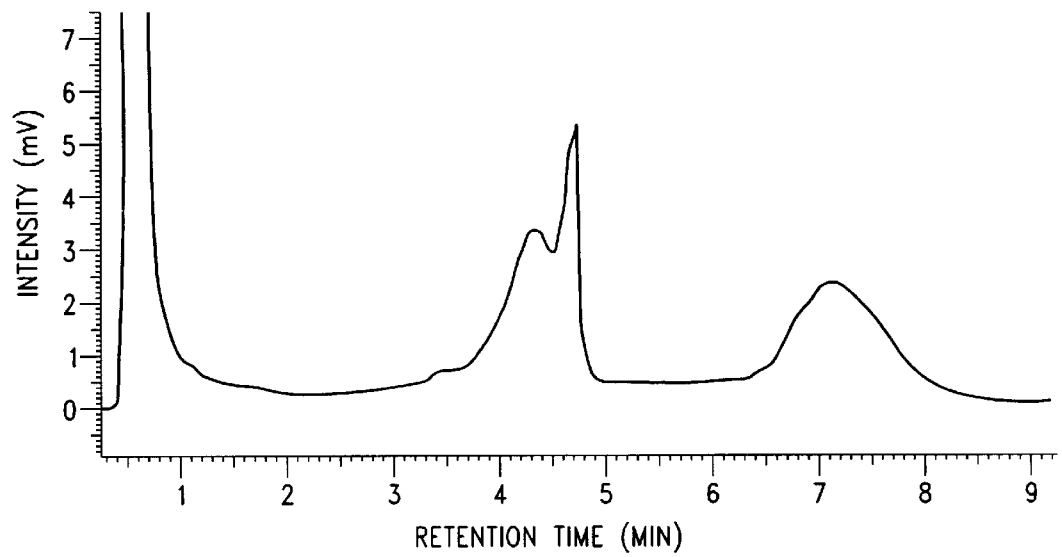
FIG. 24 is a DMIPC elution profile of a hybridized mixture containing a Lambda DNA strand containing a mutation and wild type strand.

As an example of the determination of the Mutation Separation Factor, FIG. 24 shows the resolution of the separation of the hybridized DNA mixture.

The PCR conditions used with each of the primers are described in the table below. All the components were combined and vortexed to ensure good mixing, and centrifuged. Aliquots were then distributed into PCR tubes as shown in the following table:

| COMPONENT | VOLUME |
| --- | --- |
| Pfu 10X Buffer (Cat. No. 600153-82, Stratagene, Inc., La Jolla, CA) | 5 µL |
| 100 µM dNTP Mix | 4 µL |
| Primer 1 (forward) | 7.5 µL |
| Primer 2 (reverse) | 8.5 µL |
| H$_2$O | 19.5 µL |
| Lambda DNA Template | 5 µL |
| PFUTurbo ™ (600250, Stratagene) | 0.5 µL |

The PCR tubes were placed into a thermocycler (PTC-100 Programmable Thermal Controller from MJ Research, Inc., Watertown, Mass.) and the temperature cycling program was initiated. The cycling program parameters are shown in the table below:

| STEP | TEMPERATURE | TIME |
| --- | --- | --- |
| 1 | 94° C. | 2 minutes |
| 2 | 94° C. | 1 minute |
| 3 | 58° C. | 1 minute |
| 4 | 72° C. | 1 minute |
| 5 | Go to Step 2, 34X | |
| 6 | 72° C. | 10 minutes |
| 7 | End | |

The DMIPC conditions used for the mutation detection separations are shown below:
Eluent A: 0.1 M TEAA; Eluent B: 0.1 M TEAA, 25% Acetonitrile; Flow rate: 0.90 mL/min Gradient:

| Time (min) | % A | % B |
| --- | --- | --- |
| 0.0 | 50.0 | 50.0 |
| 0.1 | 45.0 | 55.0 |
| 4.6 | 36.0 | 64.0 |
| 4.7 | 0.0 | 100.0 |
| 5.2 | 0.0 | 100.0 |
| 5.3 | 50.0 | 50.0 |
| 7.8 | 50.0 | 50.0 |

The Lambda sequence has been published by O'Conner et al. in *Biophys. J.* 74:A285 (1998) and by Garner, et al., at the Mutation Detection 97 4th International Worksh, op, Human Genome Organization, May 29-Jun. 2, 1997, Brno, Czech Republic, Poster no. 29. The 100 bp Lambda fragment sequence (base positions 32011 - 32110) was used as a standard (available from FMC Corp. available from FMC Corp. BioProducts, Rockland, Maine). The mutation was at position 32061. The chart below lists the primers used:

Primers
Forward Primer:
5'-GGATAATGTCCGGTGTCATG-3'

Reverse Primer:
3'-GGACACAGTCAAGACTGCTA-5'

Figure 23:
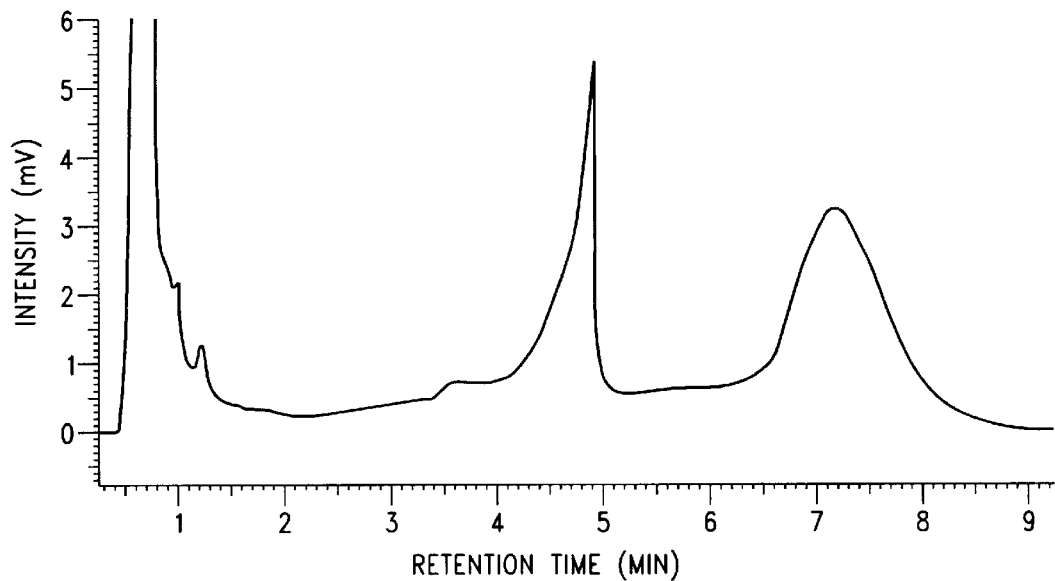
FIG. 23 is a DMIPC elution profile of a 100 bp PCR product from a wild-type strand of Lambda DNA.

FIG. 23 is a chromatogram of the wild type strand analyzed under the above conditions. The peak appearing has a retention time of 4.78 minutes and an area of 98621.

FIG. 24 is the Lambda mutation analyzed in identical conditions as FIG. 23 above. Two peaks are apparent in this chromatogram, with retention times of 4.32 and 4.68 minutes and a total area of 151246.

The Mutation Separation Factor is calculated by applying these various peak areas to the above MSF equation. Thus, using the definition stated hereinabove, MSF=(area peak 2−area peak 1)/area peak 1, the MSF would be (151246−98621)/98621, or 0.533.

EXAMPLE 18

Effect of multivalent cation decontamination measures on sample resolution by DMIPC The separation shown in FIG. 20 was obtained using a WAVE™ DNA Fragment Analysis System (Transgenomic, Inc., San Jose, Calif.) under the following conditions: Column: 50×4.6 mm i.d. containing alkylated poly(styrene-divinylbenzene) beads (DNASep®, Transgenomic, Inc.); mobile phase 0.1 M TEAA (1 M concentrate available from Transgenomic, Inc.) (Eluent A), pH 7.3; gradient: 50-53% 0.1 M TEAA and 25.0% acefonitrile (Eluent B) in 0.5 min; 53-60% B in 7 min; 60-100% B in 1.5 min; 100-50% B in 1 min; 50% B for 2 min. The flow rate was 0.9 mUmin, UV detection was at 254 nm, and the column temperature was 56° C. The sample was 2 μL (=0.2 μg DNA, DYS271 209 bp mutation standard with an A to G mutation at position 168).

FIG. 21 is the same separation as performed in FIG. 20, but after changing the guard cartridge (20×4.0 mm, chelating cartridge, part no. 530012 from Transgenomic, Inc.) and replacing the pump-valve filter (Part no. 638-1423, Transgenomic, Inc.). The guard cartridge had dimensions of 10×3.2 mm, containing iminodiacetate chelating resin of 2.5 mequiv/g capacity and 10 μm particle size, and was positioned directly in front of the injection valve.

FIG. 22 is the same separation as performed in FIG. 21, but after flushing the column for 45 minutes with 0.1 M TEAA, 25% acetonitrile, and 32 mM EDTA, at 75° C.

EXAMPLE 19

Hybridization of mutant and wild type DNA fragments

Figure 19:
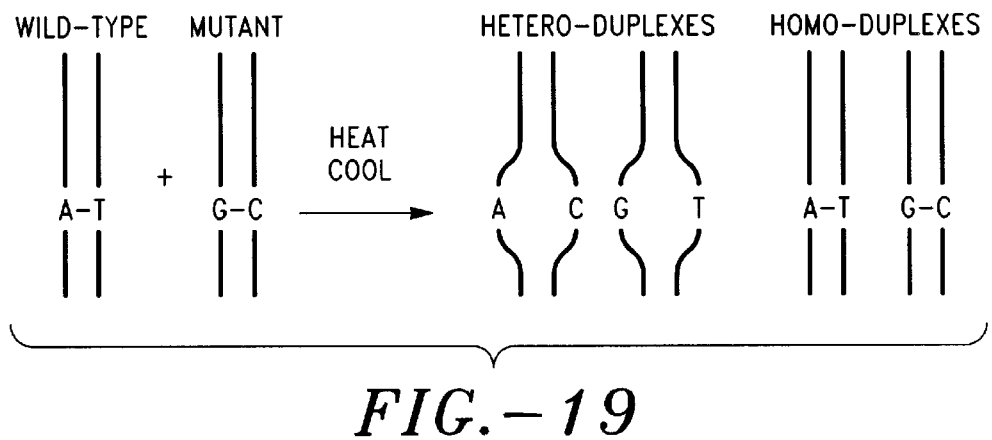
FIG. 19 shows a schematic representation of a hybridization to form a mixture of homoduplexes and heteroduplexes.

A mixture of two homoduplexes and two heteroduplexes was produced by a hybridization process. In this process, a DYS271 209 bp mutation standard containing a mixture of the homozygous mutant DNA fragment (with an A to G mutation at position 168) combined with the corresponding wild type fragment in an approximately 1:1 ratio (the mixture is available as a Mutation Standard from Transgenomic, Inc., San Jose, Calif.; the mutation is described by Seielstad et al., *Human Mol. Genet.* 3:2159 (1994)) was heated at 95° C. for 3 - 5 minutes then cooled to 25° C. over 45 minutes. The hybridization process is shown schematically in FIG. 19.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. A method for separating a mixture of polynucleotides, comprising
   a) applying a mixture of polynucleotides having up to 1500 base pairs to separation medium comprising a silica gel monolith, the monolith having separation surfaces which are coated with a hydrocarbon or non-polar hydrocarbon substituted polymer, or having substantially all polar groups reacted with a non-polar hydrocarbon or substituted hydrocarbon group, wherein said surfaces are non-polar and the monolith is substantially free from multivalent cations which are free to interfere with polynucleotide separation; and
   b) eluting said mixture of polynucleotides.

2. A method of claim 1 wherein said medium is characterized by having a DNA Separation Factor of at least 0.05.

3. A method of claim 1 wherein said medium is characterized by having a Mutation Separation Factor of at least 0.1.

4. A method of claim 1 including eluting said mixture with a mobile phase comprising a counterion agent and an organic solvent, wherein said organic solvent is water soluble.

5. A method of claim 4, wherein said solvent is selected from the group consisting of alcohol, acetonitrile, dimethylformamide, tetrahydrofuran, ester, ether, and mixtures of one or more thereof.

6. A method of claim 4 wherein said counterion agent is selected from the group consisting of lower alkyl primary amine, lower alkyl secondary amine, lower alkyl tertiary amine, lower alkyl trialkyammonium salt, quaternary ammonium salt, and mixtures of one or more thereof.

7. A method of claim 4 wherein said counterion agent is selected from the group consisting of octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, tetrabutylammonium acetate, triethylammonium hexafluoroisopropyl alcohol, and mixtures of one or more thereof.

8. A method of claim 4 wherein said counterion agent includes an anion, said anion is selected from the group comprising acetate, carbonate, phosphate, sulfate, nitrate, propionate, formate, chloride, and bromide.

9. A method of claim 1 wherein said separation is by Matched Ion Polynucleotide Chromatography.

10. The method of claim 1 wherein said medium has been subjected to an acid wash treatment in order to substantially remove multivalent cation contaminants from said surfaces.

11. The method of claim 1 wherein said medium has been subjected to treatment with EDTA in order to substantially remove multivalent cation contaminants from said surfaces.

* * * * *